(12) United States Patent
Belnoue et al.

(10) Patent No.: US 9,809,801 B2
(45) Date of Patent: Nov. 7, 2017

(54) ANTI-MYCOBACTERIAL VACCINES

(71) Applicant: Université de Genève, Genève (CH)

(72) Inventors: Elodie Anne Françoise Belnoue, Genève (CH); Stéphanie Gabrielle Darbre Abdelrahman, Lausanne (CH); Arun Thomas Kamath, Lyons (AU); Paul Lambert, Versoix (CH); Claire-Anne Siegrist-Julliard, Troinex (CH); Daniel David Pinschewer, Vésenaz (CH)

(73) Assignee: Université de Genève, Genève (CH)

( * ) Notice: Subject to any disclaimer, the term of this patent is extended or adjusted under 35 U.S.C. 154(b) by 0 days.

(21) Appl. No.: 14/775,484

(22) PCT Filed: Mar. 14, 2014

(86) PCT No.: PCT/EP2014/055144
§ 371 (c)(1),
(2) Date: Sep. 11, 2015

(87) PCT Pub. No.: WO2014/140301
PCT Pub. Date: Sep. 18, 2014

(65) Prior Publication Data
US 2016/0024476 A1    Jan. 28, 2016

Related U.S. Application Data

(60) Provisional application No. 61/793,522, filed on Mar. 15, 2013.

(51) Int. Cl.
*A61K 39/00*    (2006.01)
*A61K 39/02*    (2006.01)
(Continued)

(52) U.S. Cl.
CPC ............ *C12N 7/00* (2013.01); *A61K 35/76* (2013.01); *A61K 39/02* (2013.01); *A61K 39/04* (2013.01);
(Continued)

(58) Field of Classification Search
None
See application file for complete search history.

(56) References Cited

U.S. PATENT DOCUMENTS 5,057,540 A    10/1991  Kensil et al.
5,736,524 A *  4/1998  Content .............. A61K 31/711
                                                    435/320.1

(Continued)

FOREIGN PATENT DOCUMENTS

EP    1156118 A1    11/2001
EP    1012295 B1    10/2004
(Continued)

OTHER PUBLICATIONS

Soleimani et al.. "Expression of human tissue plasminogen activator in the trypanosomatid protozoan Leishmania tarentolae," Biotechnol. Appl. Biochem. 48: 55-61 (2007).*
(Continued)

*Primary Examiner* — Janet L Andres
*Assistant Examiner* — M. Franco Salvoza
(74) *Attorney, Agent, or Firm* — Jones Day

(57) ABSTRACT

Provided herein are genetically modified arenaviruses suitable as vaccines against mycobacterial infections. The invention also relates to pharmaceutical compositions and methods for the prevention and treatment of mycobacterial infections. Specifically, provided herein are pharmaceutical compositions, vaccines, and methods of preventing and treating infections in *Mycobacterium tuberculosis*.

3 Claims, 4 Drawing Sheets

Figure 1:
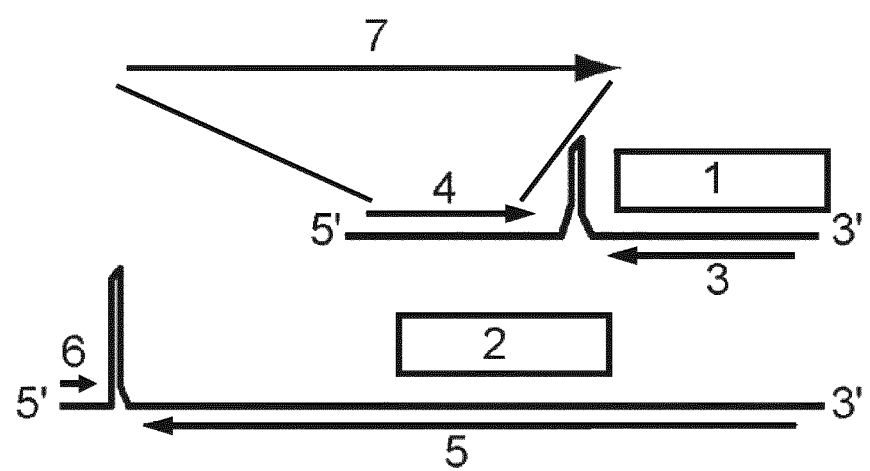

(51) Int. Cl.
  *A61K 39/12* (2006.01)
  *A61K 39/04* (2006.01)
  *C07H 21/02* (2006.01)
  *C12N 7/00* (2006.01)
  *A61K 35/76* (2015.01)

(52) U.S. Cl.
  CPC ............. *C12N 2760/10021* (2013.01); *C12N 2760/10031* (2013.01); *C12N 2760/18511* (2013.01); *C12N 2760/18534* (2013.01); *C12N 2810/85* (2013.01)

(56) References Cited

U.S. PATENT DOCUMENTS

| | | | |
|---|---|---|---|
| 5,789,245 | A | 8/1998 | Dubensky, Jr. et al. |
| 8,592,205 | B2 | 11/2013 | Pinschewer et al. |
| 9,309,289 | B2 | 4/2016 | Pinschewer et al. |
| 2005/0123517 | A1 | 6/2005 | McCray et al. |
| 2009/0041725 | A1 | 2/2009 | Neubert et al. |
| 2010/0297172 | A1* | 11/2010 | Pinschewer ............. C12N 7/00 424/204.1 |

FOREIGN PATENT DOCUMENTS

| | | | |
|---|---|---|---|
| EP | 1608393 | B1 | 2/2012 |
| WO | WO 2005/061534 | A2 | 7/2005 |
| WO | WO 2006/053871 | A2 | 5/2006 |
| WO | WO 2006/084746 | A1 | 8/2006 |
| WO | WO 2007/109812 | A2 | 9/2007 |
| WO | WO 2007/109813 | A1 | 9/2007 |
| WO | WO 2009/083210 | A1 | 7/2009 |
| WO | WO 2012/093340 | A2 | 7/2012 |

OTHER PUBLICATIONS

NCBI BLAST Search Result and Alignment for portion III of SEQ ID No. 1 (2016).*
NCBI Accession No. DQ408670.1 (Bergthaler et al.) (2006).*
Abel et al., "The novel tuberculosis vaccine, AERAS-402, induces robust and polyfunctional CD4+ and CD8+ T cells in adults," Am. J. Respir. Crit. Care Med., 181(12):1407-1417 (2010).
Altman et al., "Phenotypic analysis of antigen-specific T lymphocytes," Science, 274(5284):94-96 (1996).
Bergthaler et al., 2007, "Contributions of the lymphocytic choriomeningitis virus glycoprotein and polymerase to strain-specific differences in murine liver pathogenicity", J Gen Virol; 88(Pt 2):592-603.
Bergthaler, 2006, "Envelope exchange for the generation of live-attenuated arenavirus vaccines", PLOS Pathogen; 2(6):501-512.
Bitzer et al., 2003, "Sendai virus vectors as an emerging negative-strand RNA viral vector system", The Journal of Gene Medicine; 5:543-553.
Bonilla et al., "Practice parameter for the diagnosis and management of primary immunodeficiency," Ann. Allergy Asthma Immunol., 94(5 Suppl. 1):S1-S63 (2005).
Bonilla, "Interpretation of lymphocyte proliferation tests," Ann. Allergy Astma Immunol., 101(1):101-104 (2008).
Buchmeier et al., eds., 2007, "Arenaviridae: the viruses and their replication", Fields Virology; Philadelphia, PA, USA: Wolter Kluwer Lippincott Williams & Wilkins 2.1791-1827.
Caruso et al., "Flow cytometric analysis of activation markers on stimulated T cells and their correlation with cell proliferation," Cytometry, 27(1):1-6 (1997).
Cornu et al., 2001, "RING finger Z protein of lymphocytic choriomeningitis virus (LCMV) inhibits transcription and RNA replication of an LCMV S-segment minigenome", J Virol; 75(19):9415-9426.
Czerkinsky et al., "A solid-phase enzyme-linked immunospot (ELISPOT) assay for enumeration of specific antibody-secreting cells," J. Immunol. Methods, 65(1-2):109-121 (1983).

Dudek et al., 2006, "Replication-defective viruses as vaccines and vaccine vectors", Virology; 344:230-239.
Flatz et al., 2006, "Recovery of an arenavirus entirely from RNA polymerase I/II-driven cDNA", Proc Natl Acad Sci USA; 103(12):4663-4668.
Flatz et al., 2010, "Development of replication-defective lymphocytic choriomeningitis virus vectors for the induction of potent CD8+ T cell immunity", Nature Medicine; 16(3):339-345.
Ghanekar et al., "Gamma interferon expression in CD8+ T cells is a marker for circulating cytotoxic T lymphocytes that recognize an HLA A2-restricted epitope of human cytomegalovirus phosphoprotein pp65," Clin. Diagn. Lab. Immunol., 8(3):628-631 (2001).
Gupta et al., "Animal moddels of tuberculosis," Tuberculosis, 85(5-6):277-293 (2005).
Hass et al., 2004, "Replicon system for lassa virus", J Virol; 78(24):13793-13803.
Hicks et al., "Age-related changes in mitogen-induced lymphocyte function from birth to old age," Am. J. Clin. Pathol., 80(2):159-163 (1983).
Hutchings S et al., "The detection and enumeration of cytokine-secreting cells in mice and man and the clinical application of these assays," J. Immunol. Methods, 120(1):1-8 (1989).
Jameson et al., "The antigenic index: a novel algorithm for predicting antigenic determinants," Comput. Appl. Biosci., 4(1):181-186 (1988).
Karkhanis et al., 2007, "Mucosal vaccine vectors: replication-competent versus replication-deficient poxviruses", Current Pharmaceutical Designs; 13:2015-2023.
Kolaskar et al., "A semi-empirical method for prediction of antigenic determinants on protein antigens," FEBS Lett., 276(1-2):172-174 (1990).
Kunz et al., 2005, "Novel antiviral strategies to combat human arenavirus infections", Current Molecular Medicine, 5:735-751.
Ladguna, "Large-scale predictions of secretory proteins from mammalian genomic and EST sequences," Curr. Opin. Biotechnol., 11(1):13-18 (2000).
Lee et al., 2000, "NP and L proteins of lymphocytic choriomeningitis virus (LCMV) are sufficient for efficient transcription and replication of LCMV genomic RNA analogs", J Virol; 74(8):3470-3477.
Lee et al., 2002, "Identification of the lymphocytic choriomeningitis virus (LCMV) proteins required to rescue LCMV RNA analogs into LCMV-like particles", Journal of Virology; 76(12):6393-6397.
Liljeström et al., 2001, "Expression of proteins using Semliki Forest virus vectors", Current Protocols in Molecular Biology; Supplement 29(1994):16.20.1-16.20.16.
Loera-Arias et al., "Targeting and retention of HPV16 E7 to the endoplasmic reticulum enhances immune tumour protection," J. Cell Mol. Med., 14(4):890-894 (2010).
Lundstrom, 2002, "Alphavirus-based vaccines", Current Opinion in Molecular Therapeutics; 4(1):28-34.
Lundstrom, 2005, "Biology and application of alphaviruses in gene therapy", Gene Therapy; 12:S92-S97.
Merkler et al., 2006, "Viral déjà vu" elicits organ-specific immune disease independent of reactivity to self, J Clin Invest; 116(5):1254-1263.
Mueller et al., 2007, "Viral targeting of fibroblastic reticular cells contributes to immunosuppression and persistence during chronic infection", Proc Natl Acad Sci USA; 104(39):15430-15435.
Murali-Krishna et al., "Counting antigen-specific CD8 T cells: a reevaluation of bystander activation during viral infection," Immunity, 8(2):177-187 (1998).
Nomura et al., "Optimization of whole blood antigen-specific cytokine assays for CD4(+) T cells," Cytometry, 40(1):60-68 (2000).
Ortiz-Riano et al., "Arenavirus reverse genetics for vaccine development," J. Gen. Virol., 94(Pt 6):1175-1188 (2013).
Pellequer et al., "PREDITOP: a program for antigenicity prediction," J. Mol. Graph., 11(3):204-210, 191-192 (1993).
Perez et al., 2003, "The small RING finger protein Z drives arenavirus budding: implications for antiviral strategies", Proc Natl Acad Sci USA;100(22):12978-12983.

(56) References Cited

OTHER PUBLICATIONS

Perez et al., 2004, "Myristoylation of the RING finger Z protein is essential for arenavirus budding", J Virol; 78(20):11443-11448.
Perfetto et al., "Seventeen-colour flow cytometry: unravelling the immune system," Nat. Rev. Immunol., 4(8):648-655 (2004).
Pinschewer et al., 2003, "Recombinant lymphocytic choriomeningitis virus expressing vesicular stomatitis virus glycoprotein", Proc Natl Acad Sci USA; 100(13):7895-7900.
Pinschewer et al., 2003, "Role of the virus nucleoprotein in the regulation of lymphocytic choriomeningitis virus transcription and RNA replication", Journal of Virology; 77(6):3882-3887.
Pinschewer et al., 2004, "Kinetics of protective antibodies are determined by the viral surface antigen", J Clin Invest; 114(7):988-993.
Pinschewer et al., 2005, "Dual role of the lymphocytic choriomeningitis virus intergenic region in transcription termination and virus propagation", J Virol; 79(7):4519-4526.
Plotkin, 2008, "Determinants of Memory T cell Responses", Vaccines 5$^{th}$ Edition, Chapter 2, p. 30.
Plotkin, 2008, "Mumps vaccine", Vaccines 5$^{th}$ Edition, Chapter 20, p. 444.
Plotkin, 2008, "Rubella vaccine", Vaccines 5$^{th}$ Edition, Chapter 29, p. 745.
Polo et al., 2002, "Virus-based vectors for human vaccine applications", Drug Discovery Today; 7(13):719-727.
Querec et al., 2009, Systems biology approach predicts immunogenicity of the yellow fever vaccine in humans, Nature Immunolgy; 10(1):116-125.
Sánchez et al., 2006, "Rescue of the prototypic Arenavirus LCMV entirely from plasmid", Virology; 350:370-380.
Stoute et al., "A preliminary evaluation of a recombinant circumsporozoite protein vaccine against Plasmodium falciparum malaria.," N. Engl. J. Med., 336(2):86-91 (1997).
Suni et al., "Detection of antigen-specific T cell cytokine expression in whole blood by flow cytometry," J. Immunol. Methods, 212(1):89-98 (1998).
Takeda et al., 2003, "Protective efficacy of an AIDS vaccine, a single DNA priming followed by a single booster with a recombinant replication-defective sendai virus vector, in a macaque AIDS model", Journal of Virology; 77(17):9710-9715.
Third Party Observation, dated May 17, 2013, in European Application No. 08868316.4 (European National Stage of PCT/EP2008/010994).
Tibbetts et al., 2003, "Establishment and maintenance of gammaherpesvirus latency are independent of infective dose and route of infection", Journal of Virology; 77(13):7696-7701.
Watanabe et al., 2002, "Immunogenicity and protective efficacy of replication-incompetent influenza virus-like particles", Journal of Virology; 76(2):767-773.
Zinkernagel, 2002, "Immunity, immunopathology and vaccines against HIV?", Vaccine; 20:1913-1917.

\* cited by examiner

SEQUENCE LISTING

<160> NUMBER OF SEQ ID NOS: 13

<210> SEQ ID NO 1

<211> LENGTH: 3104
<212> TYPE: DNA
<213> ORGANISM: Artificial Sequence
<220> FEATURE:
<223> OTHER INFORMATION: rLCMV/tPA-Ag85B-TB10.4

<400> SEQUENCE: 1
gcgcaccggg gatcctaggc tttttggatt gcgctttcct ctagatcaac tgggtgtcag 60
gccctatcct acagaaggat ggatgcaatg aagagagggc tctgctgtgt gctgctgctg 120
tgtggagcag tcttcgtttc gcccagcgag atctccttct cccggccggg gctgccggtc 180
gagtacctgc aggtgccgtc gccgtcgatg ggccgcgaca tcaaggttca gttccagagc 240
ggtgggaaca actcacctgc ggtttatctg ctcgacggcc tgcgcgccca agacgactac 300
aacggctggg atatcaacac cccggcgttc gagtggtact accagtcggg actgtcgata 360
gtcatgccgg tcggcgggca gtccagcttc tacagcgact ggtacagccc ggcctgcggt 420
aaggctggct gccagactta caagtgggaa accttcctga ccagcgagct gccgcaatgg 480
ttgtccgcca acagggccgt gaagcccacc ggcagcgctg caatcggctt gtcgatggcc 540
ggctcgtcgg caatgatctt ggccgcctac cacccccagc agttcatcta cgccggctcg 600
ctgtcggccc tgctggaccc ctctcagggg atggggccta gcctgatcgg cctcgcgatg 660
ggtgacgccg gcggttacaa ggccgcagac atgtggggtc cctcgagtga cccggcatgg 720
gagcgcaacg accctacgca gcagatcccc aagctggtcg caaacaacac ccggctatgg 780
gtttattgcg ggaacggcac cccgaacgag ttgggcggtg ccaacatacc cgccgagttc 840
ttggagaact tcgttcgtag cagcaacctg aagttccagg atgcgtacaa cgccgcgggc 900
gggcacaacg ccgtgttcaa cttcccgccc aacggcacgc acagctggga gtactggggc 960
gctcagctca acgccatgaa gggtgacctg cagagttcgt taggcgccgg catgtcgcaa 1020
atcatgtaca actaccccgc gatgttgggt cacgccgggg atatggccgg atatgccggc 1080
acgctgcaga gcttgggtgc cgagatcgcc gtggagcagg ccgcgttgca gagtgcgtgg 1140
cagggcgata ccgggatcac gtatcaggcg tggcaggcac agtggaacca ggccatggaa 1200
gatttggtgc gggcctatca tgcgatgtcc agcacccatg aagccaacac catggcgatg 1260
atggcccgcg acacggccga agccgccaaa tggggcggct gaagaacagc gcctccctga 1320
ctctccacct cgaaagaggt ggagagtcag ggaggcccag agggtcttag agtgtcacaa 1380
catttgggcc tctaaaaatt aggtcatgtg gcagaatgtt gtgaacagtt ttcagatctg 1440
ggagccttgc tttggaggcg ctttcaaaaa tgatgcagtc catgagtgca cagtgcgggg 1500
tgatctcttt cttctttttg tcccttacta ttccagtatg catcttacac aaccagccat 1560
atttgtccca cactttatct tcatactccc tcgaagcttc cctggtcatt tcaacatcga 1620
taagcttaat gtccttccta ttttgtgagt ccagaagctt tctgatgtca tcggagcctt 1680
gacagcttag aaccatcccc tgcggaagag cacctataac tgacgaggtc aacccgggtt 1740
gcgcattgaa gaggtcggca agatccatgc cgtgtgagta cttggaatct tgcttgaatt 1800
gtttttgatc aacgggttcc ctgtaaaagt gtatgaactg ccctgactgt ggttggaaaa 1860
ttgctatttc cactggatca ttaaatctac cctcaatgtc aatccatgta ggagcgttgg 1920
ggtcaattcc tcccatgagg tcttttaaaa gcattgtctg gctgtagctt aagcccacct 1980
gaggtggacc tgctgctcca ggcgctggcc tgggtgagtt gactgcaggt ttctcgcttg 2040
tgagatcaat tgttgtgttt tcccatgctc tccccacaat cgatgttcta caagctatgt 2100
atggccatcc ttcacctgaa aggcaaactt tatagaggat gttttcataa gggttcctgt 2160

-continued

| | |
|---|---|
| ccccaacttg gtctgaaaca aacatgttga gttttctctt ggccccgaga actgccttca | 2220 |
| agagatcctc gctgttgctt ggcttgatca aaattgactc taacatgtta cccccatcca | 2280 |
| acagggctgc ccctgccttc acggcagcac caagactaaa gttatagcca gaaatgttga | 2340 |
| tgctggactg ctgttcagtg atgaccccca gaactgggtg cttgtctttc agcctttcaa | 2400 |
| gatcattaag atttggatac ttgactgtgt aaagcaagcc aaggtctgtg agcgcttgta | 2460 |
| caacgtcatt gagcggagtc tgtgactgtt tggccataca agccatagtt agacttggca | 2520 |
| ttgtgccaaa ttgattgttc aaaagtgatg agtctttcac atcccaaact cttaccacac | 2580 |
| cacttgcacc ctgctgaggc tttctcatcc caactatctg taggatctga gatctttggt | 2640 |
| ctagttgctg tgttgttaag ttccccatat ataccctga agcctggggc ctttcagacc | 2700 |
| tcatgatctt ggccttcagc ttctcaaggt cagccgcaag agacatcagt tcttctgcac | 2760 |
| tgagcctccc cactttcaaa acattcttct ttgatgttga ctttaaatcc acaagagaat | 2820 |
| gtacagtctg gttgagactt ctgagtctct gtaggtcttt gtcatctctc ttttccttcc | 2880 |
| tcatgatcct ctgaacattg ctgacctcag agaagtccaa cccattcaga aggttggttg | 2940 |
| catccttaat gacagcagcc ttcacatctg atgtgaagct ctgcaattct cttctcaatg | 3000 |
| cttgcgtcca ttggaagctc ttaacttcct tagacaagga catcttgttg ctcaatggtt | 3060 |
| tctcaagaca aatgcgcaat caaatgccta ggatccactg tgcg | 3104 |

```
<210> SEQ ID NO 2
<211> LENGTH: 1224
<212> TYPE: DNA
<213> ORGANISM: Artificial Sequence
<220> FEATURE:
<223> OTHER INFORMATION: tPA-Ag85B-TB10.4 cDNA sequence

<400> SEQUENCE: 2
```

| | |
|---|---|
| atggatgcaa tgaagagagg gctctgctgt gtgctgctgc tgtgtggagc agtcttcgtt | 60 |
| tcgcccagcg agatctcctt ctcccggccg gggctgccgg tcgagtacct gcaggtgccg | 120 |
| tcgccgtcga tgggccgcga catcaaggtt cagttccaga gcggtgggaa caactcacct | 180 |
| gcggtttatc tgctcgacgg cctgcgcgcc caagacgact acaacggctg gatatcaac | 240 |
| accccggcgt tcgagtggta ctaccagtcg ggactgtcga tagtcatgcc ggtcggcggg | 300 |
| cagtccagct tctacagcga ctggtacagc ccggcctgcg gtaaggctgg ctgccagact | 360 |
| tacaagtggg aaaccttcct gaccagcgag ctgccgcaat ggttgtccgc aacagggcc | 420 |
| gtgaagccca ccggcagcgc tgcaatcggc ttgtcgatgg ccggctcgtc ggcaatgatc | 480 |
| ttggccgcct accaccccca gcagttcatc tacgccggct cgctgtcggc cctgctggac | 540 |
| ccctctcagg ggatggggcc tagcctgatc ggcctcgcga tgggtgacgc cggcggttac | 600 |
| aaggccgcag acatgtgggg tccctcgagt gacccggcat gggagcgcaa cgaccctacg | 660 |
| cagcagatcc ccaagctggt cgcaaacaac accccggctat gggtttattg cgggaacggc | 720 |
| accccgaacg agttgggcgg tgccaacata cccgccgagt tcttggagaa cttcgttcgt | 780 |
| agcagcaacc tgaagttcca ggatgcgtac aacgccgcgg cgggcacaa cgccgtgttc | 840 |
| aacttcccgc caacggcac gcacagctgg gagtactggg cgctcagct caacgccatg | 900 |
| aagggtgacc tgcagagttc gttaggcgcc ggcatgtcgc aaatcatgta caactacccc | 960 |
| gcgatgttgg gtcacgccgg ggatatggcc ggatatgccg gcacgctgca gagcttgggt | 1020 |
| gccgagatcg ccgtggagca ggccgcgttg cagagtgcgt ggcagggcga taccgggatc | 1080 |

```
acgtatcagg cgtggcaggc acagtggaac caggccatgg aagatttggt gcgggcctat    1140
catgcgatgt ccagcaccca tgaagccaac accatggcga tgatggcccg cgacacggcc    1200
gaagccgcca atggggcgg ctga                                             1224
```

<210> SEQ ID NO 3
<211> LENGTH: 407
<212> TYPE: PRT
<213> ORGANISM: Artificial Sequence
<220> FEATURE:
<223> OTHER INFORMATION: tPA-Ag85B-TB10.4 amino acid sequence

<400> SEQUENCE: 3

```
Met Asp Ala Met Lys Arg Gly Leu Cys Cys Val Leu Leu Leu Cys Gly
 1               5                  10                  15

Ala Val Phe Val Ser Pro Ser Glu Ile Ser Phe Ser Arg Pro Gly Leu
            20                  25                  30

Pro Val Glu Tyr Leu Gln Val Pro Ser Pro Ser Met Gly Arg Asp Ile
        35                  40                  45

Lys Val Gln Phe Gln Ser Gly Gly Asn Asn Ser Pro Ala Val Tyr Leu
    50                  55                  60

Leu Asp Gly Leu Arg Ala Gln Asp Asp Tyr Asn Gly Trp Asp Ile Asn
65                  70                  75                  80

Thr Pro Ala Phe Glu Trp Tyr Tyr Gln Ser Gly Leu Ser Ile Val Met
                85                  90                  95

Pro Val Gly Gly Gln Ser Ser Phe Tyr Ser Asp Trp Tyr Ser Pro Ala
            100                 105                 110

Cys Gly Lys Ala Gly Cys Gln Thr Tyr Lys Trp Glu Thr Phe Leu Thr
        115                 120                 125

Ser Glu Leu Pro Gln Trp Leu Ser Ala Asn Arg Ala Val Lys Pro Thr
    130                 135                 140

Gly Ser Ala Ala Ile Gly Leu Ser Met Ala Gly Ser Ser Ala Met Ile
145                 150                 155                 160

Leu Ala Ala Tyr His Pro Gln Gln Phe Ile Tyr Ala Gly Ser Leu Ser
                165                 170                 175

Ala Leu Leu Asp Pro Ser Gln Gly Met Gly Pro Ser Leu Ile Gly Leu
            180                 185                 190

Ala Met Gly Asp Ala Gly Gly Tyr Lys Ala Ala Asp Met Trp Gly Pro
        195                 200                 205

Ser Ser Asp Pro Ala Trp Glu Arg Asn Asp Pro Thr Gln Gln Ile Pro
    210                 215                 220

Lys Leu Val Ala Asn Asn Thr Arg Leu Trp Val Tyr Cys Gly Asn Gly
225                 230                 235                 240

Thr Pro Asn Glu Leu Gly Gly Ala Asn Ile Pro Ala Glu Phe Leu Glu
                245                 250                 255

Asn Phe Val Arg Ser Ser Asn Leu Lys Phe Gln Asp Ala Tyr Asn Ala
            260                 265                 270

Ala Gly Gly His Asn Ala Val Phe Asn Phe Pro Pro Asn Gly Thr His
        275                 280                 285

Ser Trp Glu Tyr Trp Gly Ala Gln Leu Asn Ala Met Lys Gly Asp Leu
    290                 295                 300

Gln Ser Ser Leu Gly Ala Gly Met Ser Gln Ile Met Tyr Asn Tyr Pro
305                 310                 315                 320

Ala Met Leu Gly His Ala Gly Asp Met Ala Gly Tyr Ala Gly Thr Leu
                325                 330                 335
```

Gln Ser Leu Gly Ala Glu Ile Ala Val Gln Ala Leu Gln Ser
                340                 345                 350

Ala Trp Gln Gly Asp Thr Gly Ile Thr Tyr Gln Ala Trp Gln Ala Gln
            355                 360                 365

Trp Asn Gln Ala Met Glu Asp Leu Val Arg Ala Tyr His Ala Met Ser
    370                 375                 380

Ser Thr His Glu Ala Asn Thr Met Ala Met Met Ala Arg Asp Thr Ala
385                 390                 395                 400

Glu Ala Ala Lys Trp Gly Gly
                405

<210> SEQ ID NO 4
<211> LENGTH: 1146
<212> TYPE: DNA
<213> ORGANISM: Artificial Sequence
<220> FEATURE:
<223> OTHER INFORMATION: Ag85B-TB10.4 cDNA sequence

<400> SEQUENCE: 4

```
atgtcccggc cggggctgcc ggtcgagtac ctgcaggtgc cgtcgccgtc gatgggccgc      60
gacatcaagg ttcagttcca gagcggtggg aacaactcac tgcggtttta tctgctcgac     120
ggcctgcgcg cccaagacga ctacaacggc tgggatatca caccccggc gttcgagtgg     180
tactaccagt cgggactgtc gatagtcatg ccggtcggcg gcagtccag cttctacagc     240
gactggtaca gcccggcctg cggtaaggct ggctgccaga cttacaagtg gaaaccttc     300
ctgaccagcg agctgccgca atggttgtcc gccaacaggg ccgtgaagcc caccggcagc     360
gctgcaatcg gcttgtcgat ggccggctcg tcggcaatga tcttggccgc ctaccacccc     420
cagcagttca tctacgccgg ctcgctgtcg gccctgctgg accctctca ggggatgggg     480
cctagcctga tcggcctcgc gatgggtgac gccggcggtt acaaggccgc agacatgtgg     540
ggtccctcga gtaccccggc atgggagcgc aacgaccta cgcagcagat ccccaagctg     600
gtcgcaaaca cacccggct atgggtttat tgcgggaacg gcaccccgaa cgagttgggc     660
ggtgccaaca tacccgccga gttcttggag aacttcgttc gtagcagcaa cctgaagttc     720
caggatgcgt acaacgccgc gggcgggcac aacgccgtgt tcaacttccc gcccaacggc     780
acgcacagct gggagtactg gggcgctcag ctcaacgcca tgaagggtga cctgcagagt     840
tcgttaggcg ccggcatgtc gcaaatcatg tacaactacc ccgcgatgtt gggtcacgcc     900
ggggatatgg ccggatatgc cggcacgctg cagagcttgg gtgccgagat cgccgtggag     960
caggccgcgt tgcagagtgc gtggcagggc gataccggga tcacgtatca ggcgtggcag    1020
gcacagtgga accaggccat ggaagatttg gtgcgggcct atcatgcgat gtccagcacc    1080
catgaagcca acaccatggc gatgatggcc cgcgacacgg ccgaagccgc caaatggggc    1140
ggctga                                                              1146
```

<210> SEQ ID NO 5
<211> LENGTH: 381
<212> TYPE: PRT
<213> ORGANISM: Artificial Sequence
<220> FEATURE:
<223> OTHER INFORMATION: Ag85B-TB10.4 amino acid sequence

<400> SEQUENCE: 5

Met Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Asn Asn

```
                    20                  25                  30
Ser Pro Ala Val Tyr Leu Leu Asp Gly Leu Arg Ala Gln Asp Tyr
                35                  40                  45
Asn Gly Trp Asp Ile Asn Thr Pro Ala Phe Glu Trp Tyr Tyr Gln Ser
        50                  55                  60
Gly Leu Ser Ile Val Met Pro Val Gly Gly Gln Ser Ser Phe Tyr Ser
 65                  70                  75                  80
Asp Trp Tyr Ser Pro Ala Cys Gly Lys Ala Gly Cys Gln Thr Tyr Lys
                85                  90                  95
Trp Glu Thr Phe Leu Thr Ser Glu Leu Pro Gln Trp Leu Ser Ala Asn
            100                 105                 110
Arg Ala Val Lys Pro Thr Gly Ser Ala Ala Ile Gly Leu Ser Met Ala
            115                 120                 125
Gly Ser Ser Ala Met Ile Leu Ala Ala Tyr His Pro Gln Gln Phe Ile
        130                 135                 140
Tyr Ala Gly Ser Leu Ser Ala Leu Leu Asp Pro Ser Gln Gly Met Gly
145                 150                 155                 160
Pro Ser Leu Ile Gly Leu Ala Met Gly Asp Ala Gly Gly Tyr Lys Ala
                165                 170                 175
Ala Asp Met Trp Gly Pro Ser Ser Asp Pro Ala Trp Glu Arg Asn Asp
            180                 185                 190
Pro Thr Gln Gln Ile Pro Lys Leu Val Ala Asn Asn Thr Arg Leu Trp
            195                 200                 205
Val Tyr Cys Gly Asn Gly Thr Pro Asn Glu Leu Gly Gly Ala Asn Ile
        210                 215                 220
Pro Ala Glu Phe Leu Glu Asn Phe Val Arg Ser Ser Asn Leu Lys Phe
225                 230                 235                 240
Gln Asp Ala Tyr Asn Ala Ala Gly Gly His Asn Ala Val Phe Asn Phe
                245                 250                 255
Pro Pro Asn Gly Thr His Ser Trp Glu Tyr Trp Gly Ala Gln Leu Asn
            260                 265                 270
Ala Met Lys Gly Asp Leu Gln Ser Ser Leu Gly Ala Gly Met Ser Gln
            275                 280                 285
Ile Met Tyr Asn Tyr Pro Ala Met Leu Gly His Ala Gly Asp Met Ala
        290                 295                 300
Gly Tyr Ala Gly Thr Leu Gln Ser Leu Gly Ala Glu Ile Ala Val Glu
305                 310                 315                 320
Gln Ala Ala Leu Gln Ser Ala Trp Gln Gly Asp Thr Gly Ile Thr Tyr
                325                 330                 335
Gln Ala Trp Gln Ala Gln Trp Asn Gln Ala Met Glu Asp Leu Val Arg
            340                 345                 350
Ala Tyr His Ala Met Ser Ser Thr His Glu Ala Asn Thr Met Ala Met
            355                 360                 365
Met Ala Arg Asp Thr Ala Glu Ala Ala Lys Trp Gly Gly
        370                 375                 380

<210> SEQ ID NO 6
<211> LENGTH: 81
<212> TYPE: DNA
<213> ORGANISM: Artificial Sequence
<220> FEATURE:
<223> OTHER INFORMATION: tPA cDNA Sequence

<400> SEQUENCE: 6
atggatgcaa tgaagagagg gctctgctgt gtgctgctgc tgtgtggagc agtcttcgtt    60
```

```
tcgcccagcg agatctcctt c                                            81
```

<210> SEQ ID NO 7
<211> LENGTH: 27
<212> TYPE: PRT
<213> ORGANISM: Artificial Sequence
<220> FEATURE:
<223> OTHER INFORMATION: tPA amino acid sequence

<400> SEQUENCE: 7

```
Met Asp Ala Met Lys Arg Gly Leu Cys Cys Val Leu Leu Leu Cys Gly
 1               5                  10                  15

Ala Val Phe Val Ser Pro Ser Glu Ile Ser Phe
            20                  25
```

<210> SEQ ID NO 8
<211> LENGTH: 20
<212> TYPE: PRT
<213> ORGANISM: Artificial Sequence
<220> FEATURE:
<223> OTHER INFORMATION: Antigenic peptide sequence

<400> SEQUENCE: 8

```
Thr His Ser Trp Glu Tyr Trp Gly Ala Gln Leu Asn Ala Met Lys Gly
 1               5                  10                  15

Asp Leu Gln Ser
            20
```

<210> SEQ ID NO 9
<211> LENGTH: 8
<212> TYPE: PRT
<213> ORGANISM: Artificial Sequence
<220> FEATURE:
<223> OTHER INFORMATION: Antigenic peptide sequence

<400> SEQUENCE: 9

```
Ile Met Tyr Asn Tyr Pro Ala Met
 1               5
```

<210> SEQ ID NO 10
<211> LENGTH: 9
<212> TYPE: PRT
<213> ORGANISM: Artificial Sequence
<220> FEATURE:
<223> OTHER INFORMATION: Antigenic peptide sequence

<400> SEQUENCE: 10

```
Gln Ile Met Tyr Asn Tyr Pro Ala Met
 1               5
```

<210> SEQ ID NO 11
<211> LENGTH: 3376
<212> TYPE: DNA
<213> ORGANISM: Lymphocytic choriomeningitis virus
<220> FEATURE:
<223> OTHER INFORMATION: Lymphocytic choriomeningitis virus segment S,
      complete sequence

<400> SEQUENCE: 11

```
cgcaccgggg atcctaggct ttttggattg cgctttcctc tagatcaact gggtgtcagg      60
ccctatccta cagaaggatg ggtcagattg tgacaatgtt tgaggctctg cctcacatca     120
tcgatgaggt gatcaacatt gtcattattg tgcttatcgt gatcacgggt atcaaggctg     180
tctacaattt tgccacctgt gggatattcg cattgatcag tttcctactt ctggctggca     240
```

```
ggtcctgtgg catgtacggt cttaagggac ccgacattta caaaggagtt taccaattta    300
agtcagtgga gtttgatatg tcacatctga acctgaccat gcccaacgca tgttcagcca    360
acaactccca ccattacatc agtatgggga cttctggact agaattgacc ttcaccaatg    420
attccatcat cagtcacaac ttttgcaatc tgacctctgc cttcaacaaa agaccctttg    480
accacacact catgagtata gtttcgagcc tacacctcag tatcagaggg aactccaact    540
ataaggcagt atcctgcgac ttcaacaatg cataaccat ccaatacaac ttgacattct    600
cagatcgaca aagtgctcag agccagtgta gaaccttcag aggtagagtc ctagatatgt    660
ttagaactgc cttcgggggg aaatacatga ggagtggctg gggctggaca ggctcagatg    720
gcaagaccac ctggtgtagc cagacgagtt accaataccct gattatacaa aatagaacct    780
gggaaaacca ctgcacatat gcaggtcctt ttgggatgtc caggattctc ctttcccaag    840
agaagactaa gttcttcact aggagactag cgggcacatt cacctggact tgtcagact     900 cttcaggggt ggagaatcca ggtggttatt gcctgaccaa atggatgatt cttgctgcag    960
agcttaagtg tttcgggaac acagcagttg cgaaatgcaa tgtaaatcat gatgccgaat   1020
tctgtgacat gctgcgacta attgactaca acaaggctgc tttgagtaag ttcaaagagg   1080
acgtagaatc tgccttgcac ttattcaaaa caacagtgaa ttctttgatt tcagatcaac   1140
tactgatgag gaaccacttg agagatctga tgggggtgcc atattgcaat tactcaaagt   1200
tttggtacct agaacatgca aagaccggcg aaactagtgt ccccaagtgc tggcttgtca   1260
ccaatggttc ttacttaaat gagacccact tcagtgatca aatcgaacag gaagccgata   1320
acatgattac agagatgttg aggaaggatt acataaagag gcaggggagt acccccctag   1380
cattgatgga cctttctgatg tttttccacat ctgcatatct agtcagcatc ttcctgcacc   1440
ttgtcaaaat accaacacac aggcacataa aaggtggctc atgtccaaag ccacaccgat   1500
taaccaacaa aggaatttgt agttgtggtg catttaaggt gcctggtgta aaaaccgtct   1560
ggaaaagacg ctgaagaaca gcgcctccct gactctccac ctcgaaagag gtggagagtc   1620
agggaggccc agagggtctt agagtgtcac aacatttggg cctctaaaaa ttaggtcatg   1680
tggcagaatg ttgtgaacag ttttcagatc tgggagcctt gctttggagg cgctttcaaa   1740
aatgatgcag tccatgagtg cacagtgcgg ggtgatctct ttcttctttt tgtcccttac   1800
tattccagta tgcatcttac acaaccagcc atatttgtcc cacactttgt cttcatactc   1860
cctcgaagct tccctggtca tttcaacatc gataagctta atgtccttcc tattctgtga   1920
gtccagaagc tttctgatgt catcggagcc ttgacagctt gaaccatcc cctgcggaag    1980 agcacctata actgacgagg tcaacccggg ttgcgcattg aagaggtcgg caagatccat   2040
gccgtgtgag tacttggaat cttgcttgaa ttgttttga tcaacgggtt ccctgtaaaa   2100
gtgtatgaac tgcccgttct gtggttggaa aattgctatt ccactggat cattaaatct    2160 accctcaatg tcaatccatg taggagcgtt ggggtcaatt cctcccatga ggtcttttaa   2220
aagcattgtc tggctgtagc ttaagcccac ctgaggtgga cctgctgctc caggcgctgg   2280
cctgggtgaa ttgactgcag gtttctcgct tgtgagatca attgttgtgt tttcccatgc   2340
tctccccaca atcgatgttc tacaagctat gtatggccat ccttcacctg aaaggcaaac   2400
tttatagagg atgttttcat aagggttcct gtccccaact tggtctgaaa caaacatgtt   2460
gagttttctc ttgccccga gaactgcctt caagaggtcc tcgctgttgc ttggcttgat   2520
caaaattgac tctaacatgt taccccccatc caacagggct gcccctgcct tcacggcagc   2580
```

```
accaagacta aagttatagc cagaaatgtt gatgctggac tgctgttcag tgatgacccc    2640
cagaactggg tgcttgtctt tcagcctttc aagatcatta agatttggat acttgactgt    2700
gtaaagcaag ccaaggtctg tgagcgcttg tacaacgtca ttgagcggag tctgtgactg    2760
tttggccata caagccatag ttagacttgg cattgtgcca aattgattgt tcaaaagtga    2820
tgagtctttc acatcccaaa ctcttaccac accacttgca ccctgctgag gctttctcat    2880
cccaactatc tgtaggatct gagatctttg gtctagttgc tgtgttgtta agttccccat    2940 atataccoct gaagcctggg gcctttcaga cctcatgatc ttggccttca gcttctcaag    3000
gtcagccgca agagacatca gttcttctgc actgagcctc cccactttca aaacattctt    3060
ctttgatgtt gactttaaat ccacaagaga atgtacagtc tggttgagac ttctgagtct    3120
ctgtaggtct ttgtcatctc tcttttcctt cctcatgatc ctctgaacat tgctgacctc    3180
agagaagtcc aacccattca gaaggttggt tgcatcctta atgacagcag ccttcacatc    3240
tgatgtgaag ctctgcaatt ctcttctcaa tgcttgcgtc cattggaagc tcttaacttc    3300
cttagacaag gacatcttgt tgctcaatgg tttctcaaga caaatgcgca atcaaatgcc    3360
taggatccac tgtgcg                                                    3376

<210> SEQ ID NO 12
<211> LENGTH: 3377
<212> TYPE: DNA
<213> ORGANISM: Lymphocytic choriomeningitis virus
<220> FEATURE:
<223> OTHER INFORMATION: Lymphocytic choriomeningitis virus segment S,
      complete sequence

<400> SEQUENCE: 12
gcgcaccggg gatcctaggc tttttggatt gcgctttcct ctagatcaac tgggtgtcag      60
gccctatcct acagaaggat gggtcagatt gtgacaatgt tgaggctct gcctcacatc     120 atcgatgagg tgatcaacat tgtcattatt gtgcttatcg tgatcacggg tatcaaggct     180
gtctacaatt ttgccacctg tgggatattc gcattgatca gtttcctact tctggctggc     240
aggtcctgtg gcatgtacgg tcttaaggga cccgacattt acaaaggagt ttaccaattt     300
aagtcagtgg agtttgatat gtcacatctg aacctgacca tgcccaacgc atgttcagcc     360
aacaactccc accattacat cagtatgggg acttctggac tagaattgac cttcaccaat     420
gattccatca tcagtcacaa cttttgcaat ctgacctctg ccttcaacaa aaagaccttt     480
gaccacacac tcatgagtat agtttcgagc ctacacctca gtatcagagg gaactccaac     540
tataaggcag tatcctgcga cttcaacaat ggcataacca tccaatacaa cttgacattc     600
tcagatgcac aaagtgctca gagccagtgt agaaccttca gaggtagagt cctagatatg     660
tttagaactg ccttcggggg gaaatacatg aggagtggct ggggctggac aggctcagat     720
ggcaagacca cctggtgtag ccagacgagt taccaatacc tgattataca aaatagaacc     780
tgggaaaacc actgcacata tgcaggtcct tttgggatgt ccaggattct cctttcccaa     840
gagaagacta agttcctcac taggagacta gcgggcacat tcacctggac tttgtcagac     900
tcttcagggg tggagaatcc aggtggttat tgcctgacca aatggatgat tcttgctgca     960
gagcttaagt gtttcgggaa cacagcagtt gcgaaatgca atgtaaatca tgatgaagaa    1020
ttctgtgaca tgctgcgact aattgactac aacaaggctg ctttgagtaa gttcaaagag    1080
gacgtagaat ctgccttgca cttattcaaa acaacagtga attctttgat ttcagatcaa    1140
ctactgatga ggaaccactt gagagatctg atggggtgc catattgcaa ttactcaaag    1200
```

```
ttttggtacc tagaacatgc aaagaccggc gaaactagtg tccccaagtg ctggcttgtc    1260
accaatggtt cttacttaaa tgagacccac ttcagtgacc aaatcgaaca ggaagccgat    1320
aacatgatta cagagatgtt gaggaaggat tacataaaga ggcaggggag tacccccta    1380
gcattgatgg accttctgat gttttccaca tctgcatatc tagtcagcat cttcctgcac    1440
cttgtcaaaa taccaacaca caggcacata aaaggtggct catgtccaaa gccacaccga    1500
ttaaccaaca aaggaatttg tagttgtggt gcatttaagg tgcctggtgt aaaaaccgtc    1560
tggaaaagac gctgaagaac agcgcctccc tgactctcca cctcgaaaga ggtggagagt    1620
cagggaggcc cagagggtct tagagtgtca caacatttgg gcctctaaaa attaggtcat    1680
gtggcagaat gttgtgaaca gttttcagat ctgggagcct tgctttggag gcgctttcaa    1740
aaatgatgca gtccatgagt gcacagtgcg gggtgatctc tttcttcttt ttgtcccta    1800
ctattccagt atgcatctta cacaaccagc catatttgtc ccacactttg tcttcatact    1860
ccctcgaagc ttcctggtc atttcaacat cgataagctt aatgtccttc ctattctgtg    1920
agtccagaag ctttctgatg tcatcggagc cttgacagct tagaaccatc ccctgcggaa    1980
gagcacctat aactgacgag gtcaacccgg gttgcgcatt aagaggtcg gcaagatcca    2040
tgccgtgtga gtacttggaa tcttgcttga attgttttg atcaacgggt tccctgtaaa    2100
agtgtatgaa ctgcccgttc tgtggttgga aaattgctat ttccactgga tcattaaatc    2160
taccctcaat gtcaatccat gtaggagcgt tggggtcaat tcctcccatg aggtctttta    2220
aaagcattgt ctggctgtag cttaagccca cctgaggtgg acctgctgct ccaggcgctg    2280
gcctgggtga attgactgca ggtttctcgc ttgtgagatc aattgttgtg ttttcccatg    2340
ctctccccac aatcgatgtt ctacaagcta tgtatggcca tccttcacct gaaaggcaaa    2400
ctttatagag gatgttttca taggggttcc tgtccccaac ttggtctgaa acaaacatgt    2460
tgagttttct cttggccccg agaactgcct tcaagaggtc ctcgctgttg cttggcttga    2520
tcaaaattga ctctaacatg ttaccccccat ccaacagggc tgcccctgcc ttcacggcag    2580
caccaagact aaagttatag ccagaaatgt tgatgctgga ctgctgttca gtgatgaccc    2640
ccagaactgg gtgcttgtct ttcagccttt caagatcatt aagatttgga tacttgactg    2700
tgtaaagcaa gccaaggtct gtgagcgctt gtacaacgtc attgagcgga gtctgtgact    2760
gtttggccat acaagccata gttagacttg gcattgtgcc aaattgattg ttcaaaagtg    2820
atgagtcttt cacatcccaa actcttacca caccacttgc accctgctga ggctttctca    2880
tcccaactat ctgtaggatc tgagatcttt ggtctagttg ctgtgttgtt aagttcccca    2940
tatatacccc tgaagcctgg ggcctttcag acctcatgat cttggccttc agcttctcaa    3000
ggtcagccgc aagagacatc agttcttctg cactgagcct ccccactttc aaaacattct    3060
tctttgatgt tgactttaaa tccacaagag aatgtacagt ctggttgaga cttctgagtc    3120
tctgtaggtc tttgtcatct ctctttcct tcctcatgat cctctgaaca ttgctgacct    3180
cagagaagtc caacccattc agaaggttgg ttgcatcctt aatgacagca gccttcacat    3240
ctgatgtgaa gctctgcaat tctcttctca atgcttgcgt ccattggaag ctcttaactt    3300
ccttagacaa ggacatcttg ttgctcaatg gtttctcaag acaaatgcgc aatcaaatgc    3360
ctaggatcca ctgtgcg                                                  3377

<210> SEQ ID NO 13
<211> LENGTH: 7229
<212> TYPE: DNA
<213> ORGANISM: Lymphocytic choriomeningitis virus
```

<220> FEATURE:
<223> OTHER INFORMATION: Lymphocytic choriomeningitis virus segment L, complete sequence

<400> SEQUENCE: 13

| | | | | | |
|---|---|---|---|---|---|
| gcgcaccggg | gatcctaggc | gtttagttgc | gctgtttggt | tgcacaactt | tcttcgtgag | 60 |
| gctgtcagaa | gtggacctgg | ctgatagcga | tgggtcaagg | caagtccaga | gaggagaaag | 120 |
| gcaccaatag | tacaaacagg | gccgaaatcc | taccagatac | cacctatctt | ggcccttttaa | 180 |
| gctgcaaatc | ttgctggcag | aaatttgaca | gcttggtaag | atgccatgac | cactaccttt | 240 |
| gcaggcactg | tttaaacctt | ctgctgtcag | tatccgacag | gtgtcctctt | tgtaaatatc | 300 |
| cattaccaac | cagattgaag | atatcaacag | ccccaagctc | tccacctccc | tacgaagagt | 360 |
| aacaccgtcc | ggccccggcc | ccgacaaaca | gcccagcaca | agggaaccgc | acgtcaccca | 420 |
| acgcacacag | acacagcacc | caacacagaa | cacgcacaca | cacacacaca | cacacccaca | 480 |
| cgcacgcgcc | cccaccaccg | ggggcgcccc | ccccccgggg | ggcggccccc | cgggagcccg | 540 |
| ggcggagccc | cacggagatg | cccatcagtc | gatgtcctcg | gccaccgacc | cgcccagcca | 600 |
| atcgtcgcag | gacctcccct | tgagtctaaa | cctgccccc | actgtttcat | acatcaaagt | 660 |
| gctcctagat | ttgctaaaac | aaagtctgca | atccttaaag | gcgaaccagt | ctggcaaaag | 720 |
| cgacagtgga | atcagcagaa | tagatctgtc | tatacatagt | tcctggagga | ttacacttat | 780 |
| ctctgaaccc | aacaaatgtt | caccagttct | gaatcgatgc | aggaagaggt | tcccaaggac | 840 |
| atcactaatc | ttttcatagc | cctcaagtcc | tgctagaaag | actttcatgt | ccttggtctc | 900 |
| cagcttcaca | atgatatttt | ggacaaggtt | tcttccttca | aaaagggcac | ccatctttac | 960 |
| agtcagtggc | acaggctccc | actcaggtcc | aactctctca | aagtcaatag | atctaatccc | 1020 |
| atccagtatt | cttttggagc | ccaacaactc | aagctcaaga | gaatcaccaa | gtatcaaggg | 1080 |
| atcttccatg | taatcctcaa | actcttcaga | tctgatatca | agacaccat | cgttcacctt | 1140 |
| gaagacagag | tctgtcctca | gtaagtggag | gcattcatcc | aacattcttc | tatctatctc | 1200 |
| acccttaaag | aggtgagagc | atgataaaag | ttcagccaca | cctggattct | gtaattggca | 1260 |
| cctaaccaag | aatatcaatg | aaaatttcct | taaacagtca | gtattattct | gattgtgcgt | 1320 |
| aaagtccact | gaaattgaaa | actccaatac | ccctttgtg | tagttgagca | tgtagtccca | 1380 |
| cagatccttt | aaggatttaa | atgcctttgg | gtttgtcagg | ccctgcctaa | tcaacatggc | 1440 |
| agcattacac | acaacatctc | ccattcggta | agagaaccac | ccaaaaccaa | actgcaaatc | 1500 |
| attcctaaac | ataggcctct | ccacatttt | gttcaccacc | tttgagacaa | atgattgaaa | 1560 |
| ggggcccagt | gcctcagcac | catcttcaga | tggcatcatt | tctttatgag | ggaaccatga | 1620 |
| aaaattgcct | aatgtcctgg | ttgttgcaac | aaattctcga | acaaatgatt | caaaatacac | 1680 |
| ctgtttttaag | aagttcttgc | agacatccct | cgtgctaaca | acaaattcat | caaccagact | 1740 |
| ggagtcagat | cgctgatgag | aattggcaag | gtcagaaaac | agaacagtgt | aatgttcatc | 1800 |
| ccttttccac | ttaacaacat | gagaaatgag | tgacaaggat | tctgagttaa | tatcaattaa | 1860 |
| aacacagagg | tcaaggaatt | taattctggg | actccacctc | atgtttttg | agctcatgtc | 1920 |
| agacataaat | ggaagaagct | gatcctcaaa | gatcttggga | tatagccgcc | tcacagattg | 1980 |
| aatcacttgg | ttcaaattca | ctttgtcctc | cagtagcctt | gagctctcag | gctttcttgc | 2040 |
| tacataatca | catgggttta | agtgcttaag | agttaggttc | tcactgttat | tcttcccttt | 2100 |
| ggtcggttct | gctaggaccc | aaacacccaa | ctcaaaagag | ttgctcaatg | aaatacaaat | 2160 |
| gtagtcccaa | agaagaggcc | ttaaaaggca | tatatgatca | cggtgggctt | ctggatgaga | 2220 |

```
ctgtttgtca caaatgtaca gcgttatacc atcccgattg caaactcttg tcacatgatc    2280
atctgtggtt agatcctcaa gcagctttt  gatatacaga ttttccctat ttttgtttct    2340
cacacacctg cttcctagag ttttgcaaag gcctataaag ccagatgaga tacaactctg    2400
gaaagctgac ttgttgattg cttctgacag cagcttctgt gcaccccttg tgaatttact    2460
acaaagtttg ttctggagtg tcttgatcaa tgatgggatt ctttcctctt ggaaagtcat    2520
cactgatgga taaccacct  tttgtcttaa accatcctt  aatgggaaca tttcattcaa    2580
attcaaccag ttaacatctg ctaactgatt cagatcttct tcaagaccga ggaggtctcc    2640
caattgaaga atggcctcct ttttatctct gttaaatagg tctaagaaaa attcttcatt    2700
aaattcacca tttttgagct tatgatgcag tttccttaca agctttctta caacctttgt    2760
ttcattagga cacagttcct caatgagtct ttgtattctg taacctctag aaccatccag    2820
ccaatctttc acatcagtgt tggtattcag tagaaatgga tccaaaggga aattggcata    2880
ctttaggagg tccagtgttc tcctttggat actattaact agggagactg ggacgccatt    2940
tgcgatggct tgatctgcaa ttgtatctat tgtttcacaa agttgatgtg gctctttaca    3000
cttgacattg tgtagcgctg cagatacaaa ctttgtgaga gagggacttt cctccccca     3060
tacatagaat ctagatttaa attctgcagc gaacctccca gccacacttt tgggctgat     3120
aaatttgttt aacaagccgc tcagatgaga ttggaattcc aacaggacaa ggacttcctc    3180
cggatcactt acaaccaggt cactcagcct cctatcaaat aaagtgatct gatcatcact    3240
tgatgtgtaa gcctctggtc tttcgccaaa gataacacca atgcagtagt tgatgaacct    3300
ctcgctaagc aaaccataga agtcagaagc attatgcaag attccctgcc ccatatcaat    3360
aaggctggat atatgggatg gcactatccc catttcaaaa tattgtctga aaattctctc    3420
agtaacagtt gtttctgaac ccctgagaag ttttagcttc gacttgacat atgatttcat    3480
cattgcattc acaacaggaa aggggacctc gacaagctta tgcatgtgcc aagttaacaa    3540
agtgctaaca tgatctttcc cggaacgcac atactggtca tcacctagtt tgagattttg    3600
tagaaacatt aagaacaaaa atgggcacat cattggtccc catttgctgt gatccatact    3660
atagtttaag aaccccttccc gcacattgat agtcattgac aagattgcat tttcaaattc    3720
cttatcattg tttaaacagg agcctgaaaa gaaacttgaa aaagactcaa aataatcttc    3780
tattaacctt gtgaacattt ttgtcctcaa atctccaata tagagttctc tatttccccc    3840
aacctgctct ttataagata gtgcaaattt cagccttcca gagtcaggac ctactgaggt    3900
gtatgatgtt ggtgattctt ctgagtagaa gcacagattt ttcaaagcag cactcataca    3960
ttgtgtcaac gacagagctt tactaaggga ctcagaatta cttttccctct cactgattct    4020
cacgtcttct tccagtttgt cccagtcaaa tttgaaattc aagccttgcc tttgcatatg    4080
cctgtatttc cctgagtacg catttgcatt catttgcaac agaatcatct tcatgcaaga    4140
aaaccaatca ttctcagaaa agaactttct acaaaggttt tttgccatct catcgaggcc    4200
acactgatct ttaatgactg aggtgaaata caaaggtgac agctctgtgg aaccctcaac    4260
agcctcacag ataaatttca tgtcatcatt ggttagacat gatgggtcaa agtcttctac    4320
taaatggaaa gatatttctg acaagataac ttttcttaag tgagccatct tccctgttag    4380
aataagctgt aaatgatgta gtccttttgt atttgtaagt ttttctccat ctcctttgtc    4440
attggccctc ctacctcttc tgtaccgtgc tattgtggtg ttgacctttt cttcgagact    4500
tttgaagaag cttgtctctt cttctccatc aaaacatatt tctgccaggt tgtcttccga    4560
```

```
tctccctgtc tcttctccct tggaaccgat gaccaatcta gagactaact tggaaacttt    4620
atattcatag tctgagtggc tcaacttata cttttgtttt cttacgaaac tctccgtaat    4680
ttgactcaca gcactaacaa gcaatttgtt aaagtcatat tccagaagtc gttctccatt    4740
tagatgctta ttaaccacca cacttttgtt actagcaaga tctaatgctg tcgcacatcc    4800
agagttagtc atgggatcta ggctgtttag cttcttctct cctttgaaaa ttaaagtgcc    4860
gttgttaaat gaagacacca ttaggctaaa ggcttccaga ttaacacctg gagttgtatg    4920
ctgacagtca atttctttac tagtgaatct cttcatttgc tcatagaaca cacattcttc    4980
ctcaggagtg attgcttcct tggggttgac aaaaaaacca aattgacttt tgggctcaaa    5040
gaacttttca aaacatttta tctgatctgt tagcctgtca ggggtctcct ttgtgatcaa    5100 atgcacagg tatgcacat tcaacataaa ttaaatttt gcactcaaca acaccttctc    5160
accagtacca aaaatagttt ttattaggaa tctaagcagc ttatacacca ccttctcagc    5220
aggtgtgatc agatcctccc tcaacttatc cattaatgat gtagatgaaa aatctgacac    5280
tattgccatc accaaatatc tgacactctg tacctgcttt tgatttctct ttgttgggtt    5340
ggtgagcatt agcaacaata gggtcctcag tgcaacctca atgtcggtga acagtcttt    5400 caaatcagga catgatctaa tccatgaaat catgatgtct atcatattgt ataagacctc    5460
atctgaaaaa attggtaaaa agaacctttt aggatctgca tagaaggaaa ttaaatgacc    5520
atccgggcct tgtatggagt agcaccttga agattctcca gtcttctggt ataataggtg    5580
gtattcttca gagtccagtt ttattacttg gcaaaacact tctttgcatt ctaccacttg    5640
atatctcaca gaccctattt gattttgcct tagtctagca actgagctag ttttcatact    5700
gtttgttaag gccagacaaa cagatgataa tcttctcagg ctctgtatgt tcttcagctg    5760
ctctgtgctg ggttggaaat tgtaatcttc aaacttcgta taatacatta tcgggtgagc    5820
tccaattttc ataaagttct caaattcagt gaatggtatg tggcattctt gctcaaggtg    5880
ttcagacagt ccgtaatgct cgaaactcag tcccaccact aacaggcatt tttgaatttt    5940
tgcaatgaac tcactaatag atgccctaaa caattcctca aaagacacct ttctaaacac    6000
ctttgacttt tttctattcc tcaaaagtct aatgaactcc tctttagtgc tgtgaaagct    6060
taccagccta tcattcacac tactatagca acaacccacc cagtgtttat cattttttaa    6120 cccttttgaat ttcgactgtt ttatcaatga ggaaagacac aaaacatcca gatttaacaa    6180
ctgtctcctt ctagtattca acagtttcaa actcttgact ttgtttaaca tagagaggag    6240
cctctcatat tcagtgctag tctcacttcc cctttcgtgc ccatgggtct ctgcagttat    6300
gaatctcatc aaaggacagg attcgactgc ctccctgctt aatgttaaga tatcatcact    6360
atcagcaagg ttttcataga gctcagagaa ttccttgatc aagccttcag ggtttacttt    6420
ctgaaagttt ctctttaatt tcccactttc taaatctctt ctaaacctgc tgaaaagaga    6480
gtttattcca aaaaccacat catcacagct catgttgggg ttgatgcctt cgtggcacat    6540
cctcataatt tcatcattgt gagttgacct cgcatctttc agaattttca tagagtccat    6600
accggagcgc ttgtcgatag tagtcttcag ggactcacag agtctaaaat attcagactc    6660
ttcaaagact ttctcatttt ggttagaata ctccaaaagt ttgaataaaa ggtctctaaa    6720
tttgaagttt gcccactctg gcataaaact attatcataa tcacaacgac catctactat    6780
tggaactaat gtgacacccg caacagcaag gtcttccctg atgcatgcca atttgttagt    6840
gtcctctata aatttcttct caaaactggc tggagtgctc ctaacaaaac actcaagaag    6900
aatgagagaa ttgtctatca gcttgtaacc atcaggaatg ataagtggta gtcctgggca    6960
```

```
tacaattcca gactccacca aaattgtttc cacagactta tcgtcgtggt tgtgtgtgca    7020
gccactcttg tctgcactgt ctatttcaat gcagcgtgac agcaacttga gtccctcaat    7080
cagaaccatt ctgggttccc tttgtcccag aaagttgagt ttctgccttg acaacctctc    7140
atcctgttct atatagttta aacataactc tctcaattct gagatgattt catccattgc    7200
gcatcaaaaa gcctaggatc ctcggtgcg                                      7229
```

ANTI-MYCOBACTERIAL VACCINES

This application is a U.S. National Stage Application under 35 U.S.C. §371 of International Patent Application No. PCT/EP2014/055144, filed Mar. 14, 2014, which claims the benefit of U.S. provisional application No. 61/793,522, filed on Mar. 15, 2013, the entire contents of which are each incorporated herein by reference.

1. INTRODUCTION

The invention relates to genetically modified arenaviruses suitable as vaccines against mycobacterial infections. The invention also relates to pharmaceutical compositions and methods for the treatment of mycobacterial infections. Specifically, provided herein are pharmaceutical compositions, vaccines, and methods of treating infections in *Mycobacterium tuberculosis.*

2. BACKGROUND

Tuberculosis (TB) is caused by *Mycobacterium tuberculosis*. TB is contagious and spreads through the air. Around two billion people, or one third of the world's population, are estimated to be infected with the bacterium and at risk of developing the disease. About 5% of infected people gets sick with tuberculosis in the first two years after infection. The other 95% develops a latent or 'sleeping' infection, which is not contagious, but can still develop into TB later in life. The overall lifetime risk for developing TB following infection is estimated to be approximately 10%.

Pulmonary (lung) tuberculosis is the most common and most infectious form of TB worldwide. However, TB can attack any part of the body. According to the latest data of the World Health Organization (WHO), there were 8.8 million new cases of TB in 2010 (WHO report, 2011). In 2010, around 1.4 million people died from tuberculosis, equaling about 3800 deaths a day and one death every 22 seconds. In 2009 there were nearly 10 million orphan children due to TB deaths. The increased mobility of the world's population, with more people traveling across borders, intensifies the spread of the airborne infectious disease. If not treated, each person with active TB infects on average 10 to 15 people every year.

TB mainly affects young adults in their most productive years. Although poverty-related and mostly affecting developing countries, tuberculosis is prevalent in all continents. Symptoms of tuberculosis include a persistent cough, pain in the chest, coughing up blood or sputum, weakness, weight loss, chills, night sweats and fever.

Currently there is only one vaccine against tuberculosis available worldwide: Bacille Calmette-Guérin (BCG). This vaccine, used since 1921, is administered to over 100 million babies every year and can protect children from severe forms of tuberculosis. However, BCG has little to no efficacy in preventing pulmonary TB in (young) adults, the most common and most infectious form of tuberculosis. Moreover, there are serious safety concerns regarding the use of BCG in HIV infected newborns. The burden of the disease, affecting economies worldwide, is estimated at hundreds of billions of dollars annually.

Vaccines—generally accepted as and proven to be both a very efficient and cost-effective way of preventing infectious diseases—can make the difference. More effective, safe vaccines to improve or replace BCG are urgently needed as tuberculosis keeps taking its toll. Modeling studies show that without new vaccines TB can never be eliminated. New vaccines, together with more accurate diagnostics and more efficient drug therapies, would save tens of millions of lives. Vaccines will also be especially crucial in combating multidrug-resistant tuberculosis (MDR-TB) and extensively drug resistant tuberculosis (XDR-TB), forms of TB that are expensive and extremely difficult or virtually impossible to treat.

Control of Mycobacterial tuberculosis (Mtb) infection depends chiefly on cell-mediated immunity (CMI) response. It is widely accepted that antibacterial T cells exert protective effects by secreting interferon-γ (IFN-γ) and tumor necrosis factor-α (TNF-α) to stimulate bacterially infected macrophages. Mtb hides intracellulary in vacuoles of these phagocytes and escapes degradation by the lysosomal machinery. Upon cognate interaction with antibacterial T cells, however, the resulting stimulation of infected macrophages allows them to kill and degrade their intracellular pathogen. Major Histocompatibility Complex (MHC) class II-restricted CD4+ T cells have long been identified as key players in this process. More recent evidence indicates that MHC class I-restricted CD8+ T cells also play an important role in antibacterial protection.

Novel vaccination strategies should therefore aim at inducing plurifunctional (IFN-γ and TNF-α co-producing) CD4+ and CD8+ T cell responses of high magnitude. Very significant differences exist between different vector platforms, and it remains unpredictable which viral vectors can optimally fulfill these requirements.

3. SUMMARY OF THE INVENTION

The invention relates to an infectious, replication-deficient arenavirus particle comprising a nucleotide sequence encoding a mycobacterial antigen.

In certain embodiments, the mycobacterial antigen is selected from the group of mycobacteria consisting of *Mycobacterium tuberculosis, M. bovis, M. bovis* BCG, *M. africanum, M. canetti, M. caprae, M. microti, M. pinnipedii, M. avium, M. avium paratuberculosis, M. avium silvaticum, M. avium "hominissuis," M. colombiense, M. indicus pranii, M. asiaticum, M. gordonae, M. gastri, M. kansasii, M. hiberniae, M. nonchromogenicum, M. terrae, M. triviale, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. africanum, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum subsp. Acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. fallax, M. confluentis, M. flavescens, M. madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M.*

*moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. pannense, M. phocaicum, M. poriferae, M. rhodesiae, M. seoulense*, or *M. tokaiense*.

In certain embodiments, the antigen is a mycolyl transferase or a fragment thereof. For example, the mycolyl transferase used in accordance with the invention described herein may comprise of *M. tuberculosis* Ag85A, *M. tuberculosis* Ag85B, or *M. tuberculosis* Ag85C. In certain embodiments, the antigen is encoded by a gene of the esat-6 gene family. More specifically, the antigen is TB10.3, TB12.9, or TB10.4 belonging to the esat-6 gene family.

In certain embodiments, the antigen is TB10.4, Ag85B, a fragment of TB10.4, or a fragment of Ag85B. In specific embodiment, the antigen is a fusion protein between TB10.4 and Ag85B. In certain embodiments, the fusion protein comprises an amino acid sequence that is 90%, 91%, 92%, 93%, 94%, 95%, 96%, 97%, 98%, 99%, or 100% identical to SEQ ID NO:5.

In certain embodiments, the antigen is fused to an N-terminal signal peptide. In certain embodiments, the antigen comprises an amino acid sequence that is 90%, 91%, 92%, 93%, 94%, 95%, 96%, 97%, 98%, 99%, or 100% identical to SEQ ID NO:3. In specific embodiment, the N-terminal signal peptide is the signal peptide of tissue plasminogen activator.

The arenavirus used in accordance with the invention described herein is a lymphocytic choriomeningitis virus. In certain embodiments, the invention comprises a modified arenavirus in which an open reading frame of the arenavirus is deleted or functionally inactivated. In specific embodiment, the open reading frame that encodes the glycoprotein gene of the arenavirus is deleted or functionally inactivated.

The invention further relates to a virus that can amplify and express its genetic information in a cell that has been infected by the virus but is unable to produce further infectious progeny particles in a non-complementing cell. In certain embodiments, the invention relates to an infectious, replication-deficient arenavirus particle comprising a genomic segment wherein the genomic segment comprises a nucleotide sequence that is at least 90%, 91%, 92%, 93%, 94%, 95%, 96%, 97%, 98%, 99%, or 100% identical to SEQ ID NO:1 (the genomic segment is RNA, the sequence in SEQ ID NO:1 is shown for DNA; however, exchanging all thymidines ("T") in SEQ ID NO:1 for uridines ("U") provides the RNA sequence).

Also provided herein is an infectious, replication-deficient arenavirus particle comprising a genomic segment, wherein the genomic segment comprises a nucleotide sequence that is at least 90%, 91%, 92%, 93%, 94%, 95%, 96%, 97%, 98%, at least 99%, or 100% identical to the sequence of nucleotide 1639 to 3315 of SEQ ID NO:11 (the genomic segment is RNA, the sequence in SEQ ID NO:11 is shown for DNA; however, exchanging all thymidines ("T") in SEQ ID NO:11 for uridines ("U") provides the RNA sequence), and wherein the genomic segment comprises a nucleotide sequence encoding a mycobacterial antigen (the mycobacterial antigen can be fused to a signal peptide that targets the mycobacterial antigen to the endoplasmic reticulum). Also provided herein is an infectious, replication-deficient arenavirus particle comprising a genomic segment, wherein the genomic segment comprises a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1639 to 3315 of SEQ ID NO:11 (the genomic segment is RNA, the sequence in SEQ ID NO:11 is shown for DNA; however, exchanging all thymidines ("T") in SEQ ID NO:11 for uridines ("U") provides the RNA sequence), and wherein the genomic segment comprises a nucleotide sequence encoding a mycobacterial antigen (the mycobacterial antigen can be fused to a signal peptide that targets the mycobacterial antigen to the endoplasmic reticulum).

Also provided herein is an infectious, replication-deficient arenavirus particle comprising a genomic segment, wherein the genomic segment comprises a nucleotide sequence that is at least 90%, 91%, 92%, 93%, 94%, 95%, 96%, 97%, 98%, at least 99%, or 100% identical to the sequence of nucleotide 1640 to 3316 of SEQ ID NO:12 (the genomic segment is RNA, the sequence in SEQ ID NO:12 is shown for DNA; however, exchanging all thymidines ("T") in SEQ ID NO:12 for uridines ("U") provides the RNA sequence), and wherein the genomic segment comprises a nucleotide sequence encoding a mycobacterial antigen (the mycobacterial antigen can be fused to a signal peptide that targets the mycobacterial antigen to the endoplasmic reticulum). Also provided herein is an infectious, replication-deficient arenavirus particle comprising a genomic segment, wherein the genomic segment comprises a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1640 to 3316 of SEQ ID NO:12 (the genomic segment is RNA, the sequence in SEQ ID NO:12 is shown for DNA; however, exchanging all thymidines ("T") in SEQ ID NO:12 for uridines ("U") provides the RNA sequence), and wherein the genomic segment comprises a nucleotide sequence encoding a mycobacterial antigen (the mycobacterial antigen can be fused to a signal peptide that targets the mycobacterial antigen to the endoplasmic reticulum).

In another aspect, provided herein are composition, e.g., pharmaceutical, immunogenic or vaccine compositions, comprising a virus described herein and a pharmaceutically inactive carrier.

In a further aspect, provided herein are methods of treating or preventing a mycobacterial infection in a patient, comprising administering to the patient a virus, a pharmaceutical composition, a immunogenic composition, or a vaccine described herein. In yet another aspect, provided herein are use of a virus, a pharmaceutical composition, a immunogenic composition, or a vaccine described herein for the treatment or prevention of a mycobacterial infection in a patient. In specific embodiment, the mycobacterial infection is an infection with *M. tuberculosis*.

3.1 Conventions and Abbreviations tPA Tissue plasminogen activator
Mtb *Mycobacterium tuberculosis*
TB Tuberculosis
LCMV Lymphocytic choriomeningitis virus
MHC Major Histocompatibility Complex
ORF Open Reading Frame
GP Glycoprotein
Z Matrix Protein
NP Nucleoprotein
UTR Untranslated region
CD8 Cluster of Differentiation 8
CD4 Cluster of Differentiation 4
IFN-γ Interferon-γ tumor
TNF-α Tumor necrosis factor-α
CMI Cell-mediated immunity MDR-TB Multidrug-resistant Tuberculosis
XDR-TB Extensively Drug Resistant Tuberculosis

4. DESCRIPTION OF THE SEQUENCE LISTING

SEQ ID No. 1 is the nucleotide sequence of rLCMV/tPA-Ag85B-TB10.4 genomic segment. The genomic segment is RNA, the sequence in SEQ ID NO:1 is shown for DNA; however, exchanging all thymidines ("T") in SEQ ID NO:1 for uridines ("U") provides the RNA sequence.

SEQ ID No. 2 is the nucleotide sequence for tPA-Ag85B-TB10.4 cDNA.

SEQ ID No. 3 is the amino acid sequence for tPA-Ag85B-TB10.4.

SEQ ID No. 4 is the nucleotide sequence for Ag85B-TB10.4 cDNA.

SEQ ID No. 5 is the amino acid sequence for Ag85B-TB10.4.

SEQ ID No. 6 is the nucleotide sequence for tPA cDNA including a six nucleotide linker.

SEQ ID No. 7 is the amino acid sequence for tPA.

SEQ ID No. 8 is the amino acid sequence of an antigenic peptide for some H2-IA$^b$-restricted CD4+ T cell.

SEQ ID No. 9 is the amino acid sequence of an antigenic peptide for some H-2K$^b$-restricted CD8+ T cell used for synthesis of MHC class I dextramers.

SEQ ID No. 10 is the amino acid sequence of an antigenic peptide for some H-2K$^b$-restricted CD8+ T cell used for restimulation prior to intracellular staining of cytokines by flow cytometry.

SEQ ID NO:11 is the lymphocytic choriomeningitis virus segment S, complete sequence. The genomic segment is RNA, the sequence in SEQ ID NO:11 is shown for DNA; however, exchanging all thymidines ("T") in SEQ ID NO:11 for uridines ("U") provides the RNA sequence.

SEQ ID NO:12 is the lymphocytic choriomeningitis virus clone 13 segment S, complete sequence (GenBank: DQ361065.2). The genomic segment is RNA, the sequence in SEQ ID NO:12 is shown for DNA; however, exchanging all thymidines ("T") in SEQ ID NO:12 for uridines ("U") provides the RNA sequence.

SEQ ID NO:13 is the lymphocytic choriomeningitis virus clone 13 segment L, complete sequence (GenBank: DQ361066.1). The genomic segment is RNA, the sequence in SEQ ID NO:13 is shown for DNA; however, exchanging all thymidines ("T") in SEQ ID NO:13 for uridines ("U") provides the RNA sequence.

5. BRIEF DESCRIPTION OF THE FIGURES

FIG. 1: Schematic representation of the genome of wild type arenaviruses. The wild type arenavirus genome consists of a short (1; ~3.4 kb) and a large (2; ~7.2 kb) RNA segment. The short segment carries the open reading frames encoding the nucleoprotein NP (3) and glycoprotein GP (4) genes. The large segment encodes the RNA-dependent RNA polymerase L (5) and the matrix protein Z (6) genes. Wild type arenaviruses can be rendered replication-deficient to generate vaccine vectors by substituting the glycoprotein gene for antigens of choice (7), against which immune responses are to be induced.

Figure 2:
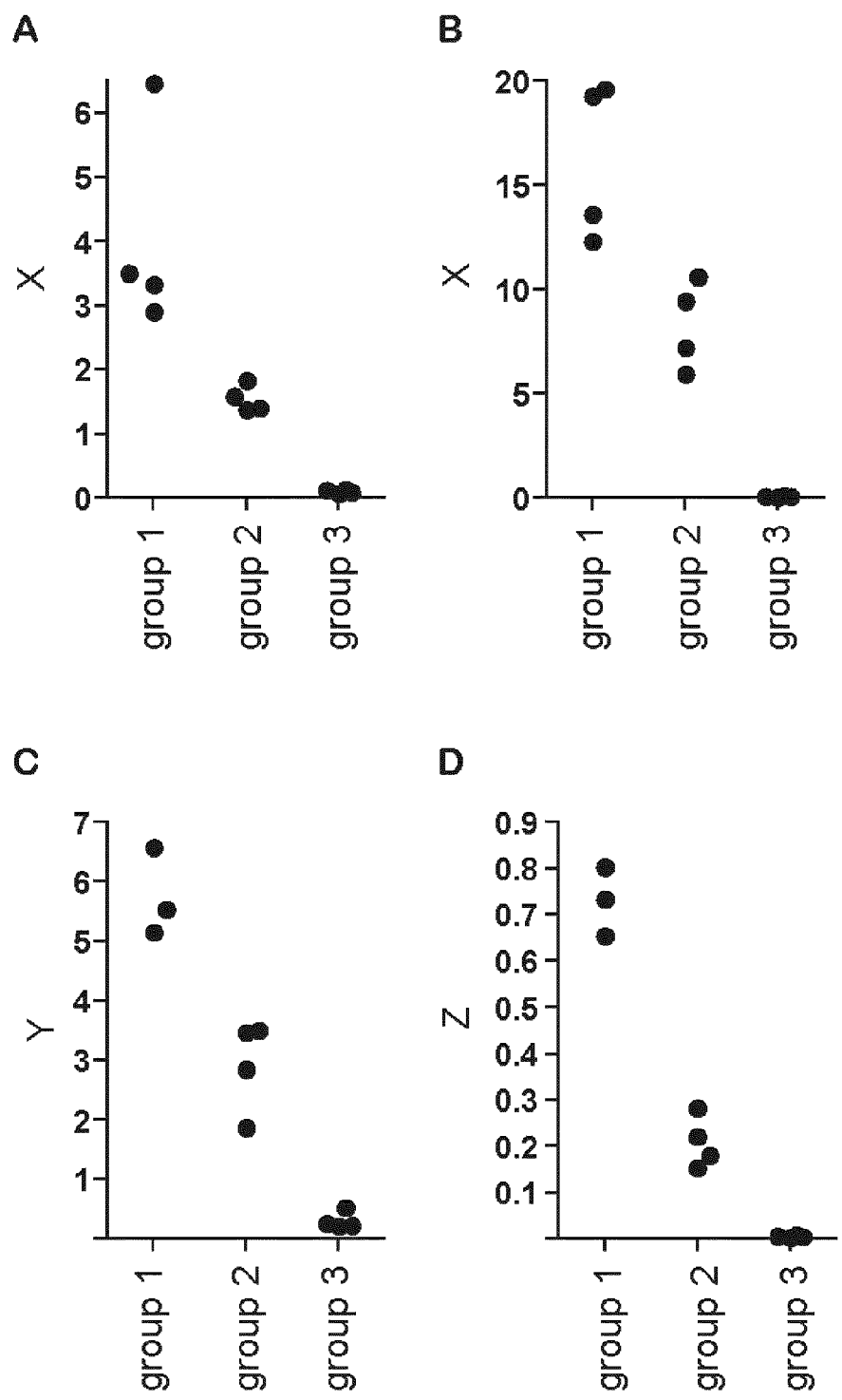

FIG. 2: Comparison of immunogenicity of rLCMV/tPA-Ag85B-TB10.4 and rLCMV/Ag85B-TB10.4 vaccine vectors in mice. On day 0 of the experiment, C57BL/6 mice were immunized with 2×10$^5$ PFU of either rLCMV/tPA-Ag85B-TB10.4 (group 1) or rLCMV/Ag85B-TB10.4 (group 2) intravenously. Control mice were not immunized (group 3). The same immunization was repeated on day 28. On day 27 (panel A) and on day 38 (panel B) TB10.4 (IMYNYPAM)-specific CD8+ T cells were measured in peripheral blood by flow cytometry using MHC class I dextramers. The Dextramer-binding cells are expressed as percentage of the total CD8+ population (X in panels A and B). On day 56 of the experiment, the animals were euthanized and single cell suspensions were prepared from the spleen of the animals. These cells were stimulated with the TB10.4-derived QIMYNYPAM peptide comprising of SEQ ID NO:10 and the Ag85B-derived THSWEYWGAQLNAMKGDLQS peptide comprising of SEQ ID NO: 8 to determine antigen-specific interferon-γ (IFN-γ) and tumor necrosis factor-α (TNF-α) co-producing CD8+ (panel C), as well as IFN-γ and TNF-α co-producing CD4+ T cells (panel D), respectively. For this, standard intracellular cytokine staining and flow cytometry techniques were used. IFN-γ and TNF-α co-producing cells amongst total CD8+ T cells (Y in panel C) or amongst total CD4+ T cells (Z in panel D) are expressed as a percentage. Symbols represent individual mice. Group 1 and group 2 mice were significantly different in all measurements as determined using unpaired two-tailed student's t-test (p=0.0226, p=0.0108, p=0.0044, p=0.0001 in panels A-D, respectively).

Figure 3:
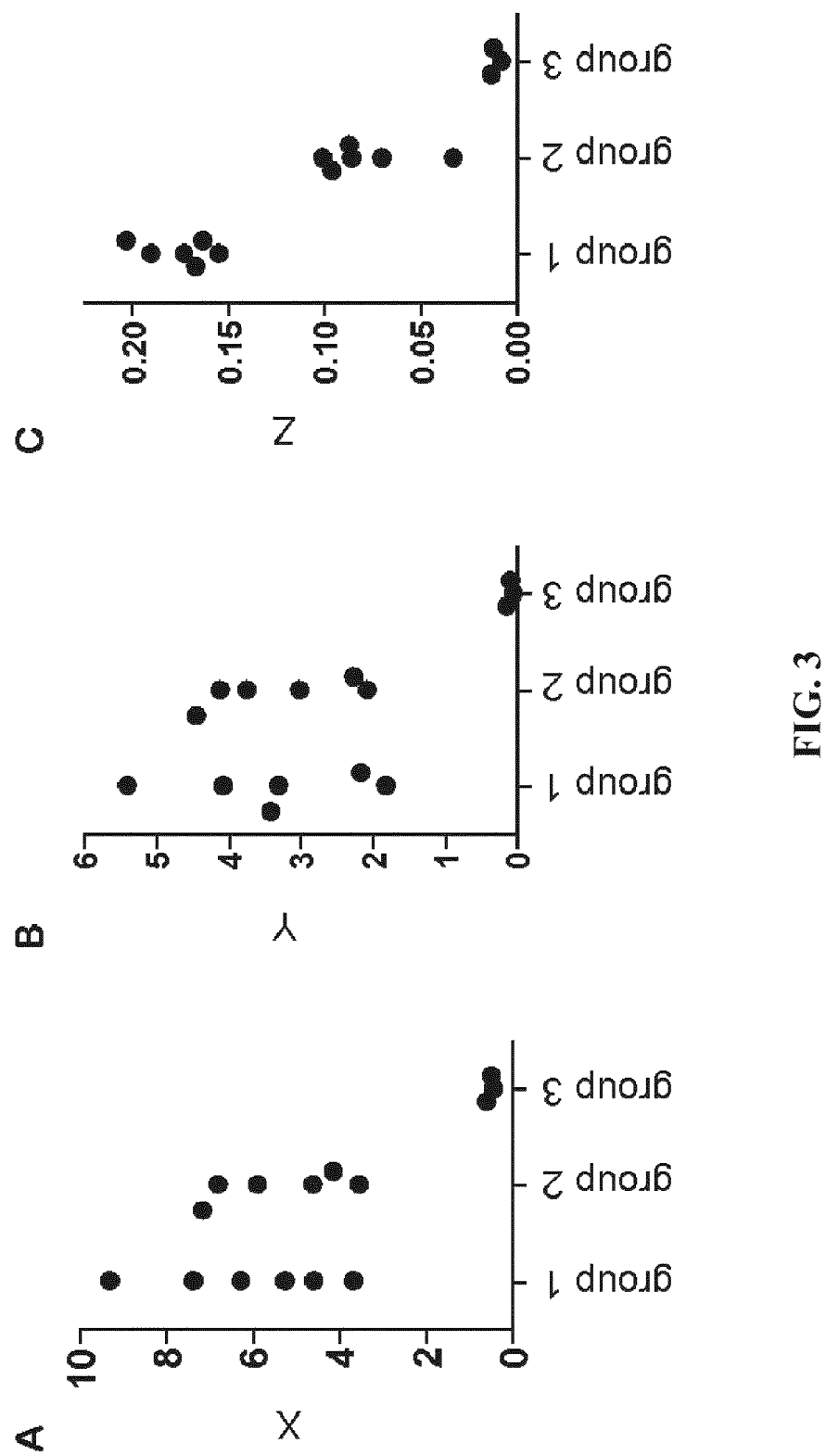

FIG. 3: Comparison of immunogenicity of rLCMV/tPA-Ag85B-TB10.4 vaccine vector administered by intravenous or subcutaneous routes. On day 0 of the experiment, C57BL/6 mice were immunized with 10$^5$ PFU of rLCMV/tPA-Ag85B-TB10.4 either via the intravenous route (group 1) or by the subcutaneous route (group 2). Control mice were not immunized (group 3). On day 11, the animals were euthanized and single cell suspensions were prepared from the spleen of these animals. TB10.4 (IMYNYPAM (SEQ ID NO:9))-specific CD8+ T cells were measured by flow cytometry using MHC class I dextramers. The Dextramer-binding cells are expressed as percentage of the total CD8+ population (X in panels A). The spleen cells were also stimulated with TB10.4-derived QIMYNYPAM peptide comprising of SEQ ID NO:10 and the Ag85B-derived THSWEYWGAQLNAMKGDLQS peptide comprising of SEQ ID NO: 8 to determine antigen-specific IFN-γ producing CD8+ (panel B), as well as IFN-γ and TNF-α co-producing CD4+ T cells (panel C), respectively. For this, standard intracellular cytokine staining and flow cytometry techniques were used. Epitope-specific IFN-γ producing CD8+ T cell within the total CD8+ T cells (Y in panel B), as well as IFN-γ and TNF-α co-producing cells amongst total CD4+ T cells (Z in panel C), are expressed as a percentage. Symbols represent individual mice.

Figure 4:
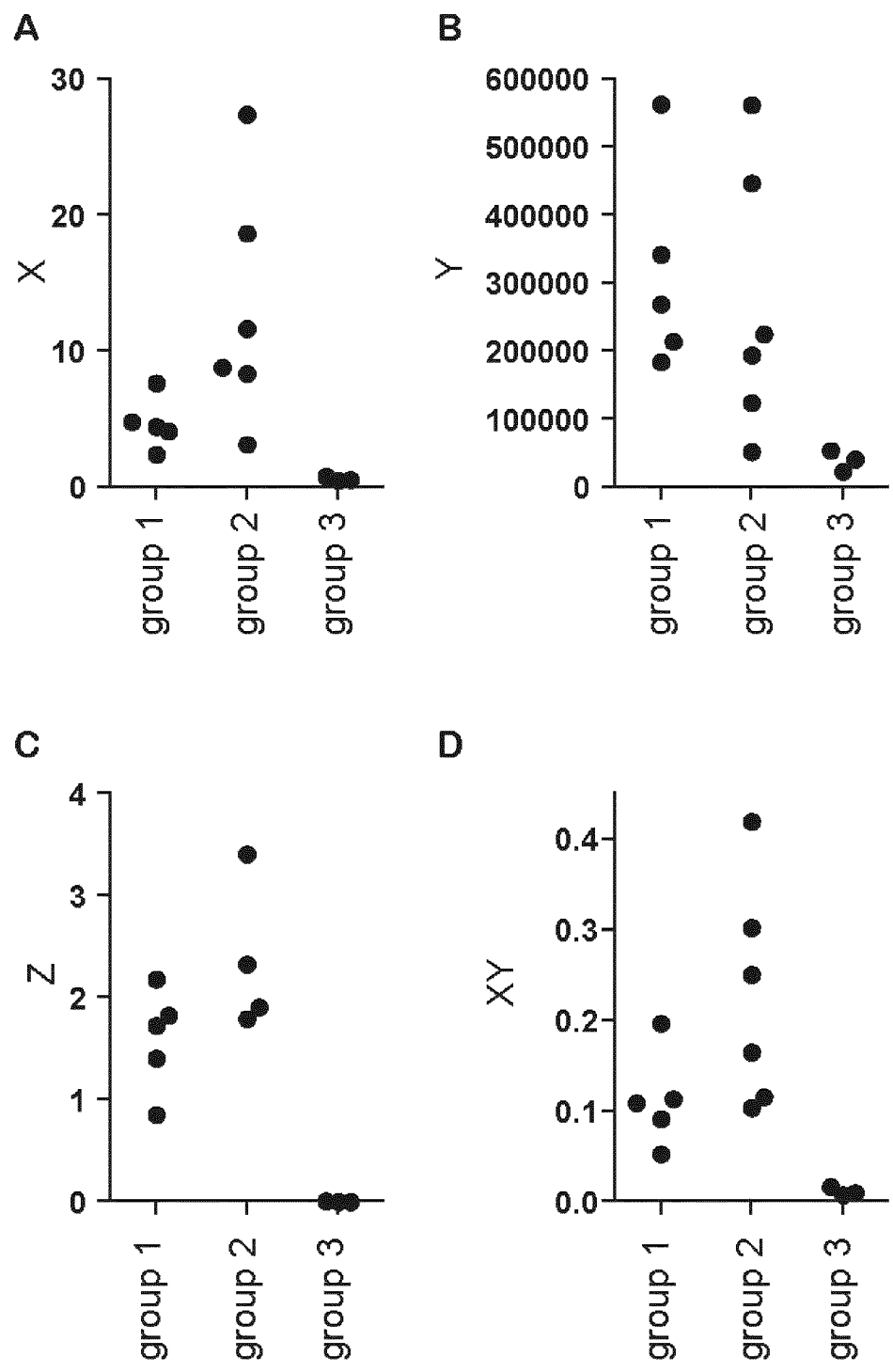

FIG. 4: Immunization studies with rLCMV/tPA-Ag85B-TB10.4 vaccine vector in adult and 1-week-old mice. On day 0 of the experiment, adult (group 1) and 1-week-old (group 2) C57BL/6 mice were immunized with 10$^5$ PFU of rLCMV/tPA-Ag85B-TB10.4 via the subcutaneous route. On day 10, the animals were euthanized and single cell suspensions were prepared from the spleen of these animals. TB10.4 (IMYNYPAM (SEQ ID NO:9))-specific CD8+ T cells were measured by flow cytometry using MHC class I dextramers. The Dextramer-binding cells are expressed as percentage of the total CD8+ population (X in panels A) or as total number of Dextramer-binding CD8+ cells in spleen (Y in panel B). These spleen cells were also stimulated with the TB10.4-derived QIMYNYPAM peptide comprising of SEQ ID NO:10 and the Ag85B-derived THSWEYWGAQL-NAMKGDLQS peptide comprising of SEQ ID NO: 8 to determine antigen-specific interferon-γ (IFN-γ) and tumor necrosis factor-α (TNF-α) co-producing CD8+ (panel C), as well as IFN-γ and TNF-α co-producing CD4+ T cells (panel D), respectively. For this, standard intracellular cytokine staining and flow cytometry techniques were used. IFN-γ and TNF-α co-producing cells amongst total CD8+ T cells (Z in panel C) or amongst total CD4+ T cells (XY in panel D) are expressed as a percentage. Symbols represent individual mice.

6. DETAILED DESCRIPTION OF THE INVENTION

Provided herein are methods and compositions for the treatment or prevention of infections of a subject with a *mycobacterium*. More specifically, provided herein are infectious, replication-deficient arenaviruses that comprise a nucleotide sequence encoding a mycobacterial antigen. These viruses can be administered to a subject for the treatment or prevention of a mycobacterial infection. The generation of infectious, replication-deficient arenavirus vectors for use with the present invention is described in more detail in Section 6.3.

Provided herein is a genetically modified arenavirus, where the arenavirus:
 i) is infectious;
 ii) cannot form infectious progeny virus in a non-complementary cell (i.e., a cell that does not express the functionality that is missing from the replication-deficient arenavirus and causes it to be replication-deficient);
 iii) is capable of replicating its genome and expressing its genetic information; and
 iv) encodes a mycobacterial antigen or a fragment thereof.

A genetically modified arenavirus described herein is infectious, i.e., it can attach to a host cell and release its genetic material into the host cell. A genetically modified arenavirus described herein is replication-deficient, i.e., the arenavirus is unable to produce further infectious progeny particles in a non-complementary cell. In particular, the genome of the arenavirus is modified (e.g., by deletion or functional inactivation of an open reading frame) such that a virus carrying the modified genome can no longer produce infectious progeny viruses. A non-complementary cell is a cell that does not provide the functionality that has been eliminated from the replication-deficient arenavirus by modification of its genome (e.g., if the open reading frame encoding the GP protein is deleted or functionally inactivated, a non-complementary cell does not provide the GP protein). However, a genetically modified arenavirus provided herein is capable of producing infectious progeny viruses in complementing cells. Complementing cells are cells that provide the functionality that has been eliminated from the replication-deficient arenavirus by modification of its genome (e.g., if the open reading frame encoding the GP protein is deleted or functionally inactivated, a complementing cell does provide the GP protein). A genetically modified arenavirus described herein amplify and express its genetic information in a cell that has been infected by the virus. A genetically modified arenavirus provided herein comprises a nucleotide sequence that encodes a mycobacterial antigen such as the mycobacterial antigens described in Section 6.2.

In certain embodiments, provided herein is a genetically modified arenavirus in which an open reading frame (ORF) of the arenavirus genome is deleted or functionally inactivated such that the resulting virus cannot produce further infectious progeny virus particles. An arenavirus particle comprising a genetically modified genome in which an open reading frame (ORF) deleted or functionally inactivated can be produced in complementing cells (i.e., in cells that express the arenaviral open reading frame that has been deleted or functionally inactivated)(see Section 6.3). The genetic material of the resulting arenavirus particles can be transferred upon infection of a host cell into the host cell, wherein the genetic material can be expressed and amplified. In addition, the genome of the genetically modified arenavirus particles provided herein encodes a mycobacterial antigen that can be expressed in the host cell.

In certain embodiments, the ORF that encodes the glycoprotein (GP) gene of the arenavirus is deleted to generate a replication-deficient arenavirus for use with the present invention. In a specific embodiment, the replication-deficient arenavirus comprises a genomic segment comprising a nucleotide sequence encoding a mycobacterial antigen. In certain embodiments, the antigen is fused to an N-terminal signal peptide that targets the mycobacterial antigen to the endoplasmic reticulum (ER) of the cell that is infected with the arenavirus. Thus, in certain embodiments, a genetically modified arenavirus particle provided herein comprises a genomic segment that a) has a deletion or functional inactivation of an open reading frame that is present in the wild type form of the genomic segment; and b) encodes (either in sense or antisense) a mycobacterial antigen (see Section 6.3).

In certain embodiments, the antigen encoded by the nucleic acid that is inserted into the genome of replication-deficient arenavirus can encode, for example, a mycobacterial antigen including, but not limited to, TB10.4, Ag85B, a fragment of TB10.4, or a fragment of Ag85B. In certain embodiments, the N-terminal signal peptide fused to the antigens described herein is the signal peptide of tissue plasminogen activator. More detailed description of the antigens and the signal peptides described herein is provided in Section 6.2.

In certain embodiments, the arenaviruses used according to the invention described herein can be Old World viruses, for example, Lymphocytic choriomeningitis virus (LCMV). More detailed description of the arenaviruses described herein is provided in Section 6.1.

Provided herein are nucleic acids encoding the genome of such replication-deficient arenaviruses. In certain aspects, an infectious, replication-deficient arenavirus particle comprises a genomic segment comprising a nucleotide sequence of SEQ ID NO:1. Provided herein are LCMV-based vector systems comprising one or two of the vector plasmids described herein. Also provided herein are cell lines, cultures and methods of culturing cells infected with nucleic acids, vectors, and compositions provided herein. More detailed description of the nucleic acids, vector systems and cell lines described herein is provided in Section 6.4.

The invention relates to such genetically modified replication-deficient arenaviruses suitable as vaccines and to methods of using such arenaviruses in vaccination and treatment or prevention of infections by mycobacteria. More detailed description of methods of using such arenaviruses described herein is provided in Section 6.5.

6.1 Infectious, Replication-Deficient Arenavirus Vectors Expressing a Mycobacterial Antigen Arenaviruses for use with the methods and compositions provided herein can be of Old World viruses, for example Lassa virus, Lymphocytic choriomeningitis virus (LCMV), Mobala virus, Mopeia virus, or Ippy virus, or New World viruses, for example Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Bear Canyon virus, or Whitewater Arroyo virus. The genetically modified arenavirus can be generated as described in Section 6.3.

The wild type arenavirus genome consists of a short (1; ~3.4 kb) and a large (2; ~7.2 kb) RNA segment. The short segment carries the open reading frames encoding the nucleoprotein NP (3) and glycoprotein GP (4) genes. The large segment encodes the RNA-dependent RNA polymerase L (5) and the matrix protein Z (6) genes. Wild type arenaviruses can be rendered replication-deficient to generate vaccine vectors by substituting the glycoprotein gene for mycobacterial antigens (7), against which immune responses are to be induced.

Infectious, replication-deficient arenavirus vectors expressing a mycobacterial antigen can be used to immunize (in a preventive manner) or treat (in an immunotherapeutic manner) subjects against mycobacterial infections. In a specific embodiment, provided here is an infectious, replication-deficient arenavirus vector expressing a mycobacterial antigen that can be used to immunize (in a preventive manner) or treat (in an immunotherapeutic manner) subjects against an infection with Mycobaterium tuberculosis.

Arenavirus disease and immunosuppression in wild type arenavirus infection are known to result from unchecked viral replication. By abolishing replication, i.e., the ability to produce infectious progeny virus particles, of arenavirus vectors by deleting from their genome, e.g., the Z gene which is required for particle release, or the GP gene which is required for infection of target cells, the total number of infected cells can be limited by the inoculum administered, e.g., to a vaccinee, or accidentally transmitted to personnel involved in medical or biotechnological applications, or to animals. Therefore, abolishing replication of arenavirus vectors prevents pathogenesis as a result of intentional or accidental transmission of vector particles. In this invention, one important aspect consists in exploiting the above necessity of abolishment of replication in a beneficial way for the purpose of expressing a mycobacterial antigen.

In certain embodiments, an arenavirus particle is rendered replication deficient by genetic modification of its genome. Such modifications to the genome can include:
  deletion of an open reading frame (e.g., the open reading frame encoding the GP, NP, L, or Z protein);
  functional inactivation of an open reading frame (e.g., the open reading frame encoding the GP, NP, L, or Z protein). For example, this can be achieved by introducing a missense or a nonsense mutation.
  mutagenesis of one of the 5' or 3' termini of one of the genomic segments;
  mutagenesis of an intergenic region (i.e., of the L or the S genomic segment).

In certain embodiments, an infectious, replication-deficient arenavirus expressing a mycobacterial antigen described herein is a Lymphocytic choriomeningitis virus (LCMV) wherein the S segment of the virus is modified by substituting the open reading frame encoding the GP protein is replaced with an open reading frame encoding a mycobacterial antigen (e.g., an antigen of *Mycobacterium tuberculosis*). In certain specific embodiments, the mycobacterial antigen is fused to a signal peptide that targets the mycobacterial antigen to the endoplasmic reticulum.

In certain embodiments, the wild type arenavirus vector genome (FIG. 1) can be designed to retain at least the essential regulatory elements on the 5' and 3' untranslated regions (UTRs) of both segments, and/or also the intergenic regions (IGRs). Without being bound by theory, the minimal transacting factors for gene expression in infected cells remain in the vector genome as open reading frames that can be expressed, yet they can be placed differently in the genome and can be placed under control of a different promoter than naturally, or can be expressed from internal ribosome entry sites. In certain embodiments, the nucleic acid encoding a mycobacterial antigen is transcribed from one of the endogenous arenavirus promoters (i.e., 5' UTR, 3' UTR of the S segment, 5' UTR, 3' UTR of the L segment). In other embodiments, the nucleic acid encoding a mycobacterial antigen is expressed from a heterologous introduced promoter sequences that can be read by the viral RNA-dependent RNA polymerase, by cellular RNA polymerase I, RNA polymerase II or RNA polymerase III, such as duplications of viral promoter sequences that are naturally found in the viral UTRs, the 28S ribosomal RNA promoter, the beta-actin promoter or the 5S ribosomal RNA promoter, respectively. In certain embodiments ribonucleic acids coding for mycobacterial antigens are transcribed and translated either by themselves or as read-through by fusion to arenavirus protein open reading frames, and expression of proteins in the host cell may be enhanced by introducing in the viral transcript sequence at the appropriate place(s) one or more, e.g., two, three or four, internal ribosome entry sites.

In certain embodiments, described herein is an arenavirus particle (e.g., LCMV) in which the open reading frame encoding the GP of the S genomic segment is substituted with a nucleotide sequence encoding:
  A signal peptide for targeting to the endoplasmic reticulum fused to a mycobacterial antigen; or
  A signal peptide for targeting to the endoplasmic reticulum fused to a mycolyl transferase of a *mycobacterium* or a fragment thereof; or
  A signal peptide for targeting to the endoplasmic reticulum fused to *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C; or
  A signal peptide for targeting to the endoplasmic reticulum fused to a gene product of a gene of the esat-6 gene family, or a fragment of at least 10, 15, 20, 25, 50, 75, or at least 100 amino acids of a gene product of a gene of the esat-6 gene family; or
  A signal peptide for targeting to the endoplasmic reticulum fused to (i) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C and (ii) a gene product of a gene of the esat-6 gene family, or a fragment of at least 10, 15, 20, 25, 50, 75, or at least 100 amino acids of a gene product of a gene of the esat-6 gene family; or
  In the following order from N-terminus to C-terminus: a signal peptide for targeting to the endoplasmic reticulum fused to (i) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C and (ii) a gene product of a gene of the esat-6 gene family, or a fragment of at least 10, 15, 20, 25, 50, 75, or at least 100 amino acids of a gene product of a gene of the esat-6 gene family; or
  In the following order from N-terminus to C-terminus: a signal peptide for targeting to the endoplasmic reticulum fused to (i) a gene product of a gene of the esat-6 gene family, or a fragment of at least 10, 15, 20, 25, 50, 75, or at least 100 amino acids of a gene product of a gene of the esat-6 gene family; and (ii) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C.

6.2 Mycobacterial Antigens

In certain embodiments, antigens for use with the methods and compositions described herein are mycobacterial antigens.

In certain embodiments, the mycobacterial antigen is an antigen of *Mycobacterium tuberculosis, M. bovis, M. bovis* BCG, *M. africanum, M. canetti, M. caprae, M. microti, M. pinnipedii, M. avium, M. avium paratuberculosis, M. avium silvaticum, M. avium "hominissuis," M colombiense, M. indicus pranii, M. asiaticum, M. gordonae, M. gastri, M. kansasii, M. hiberniae, M. nonchromogenicum, M. terrae, M. triviale, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. africanum, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intennedium, M. abscessus, M. chelonae, M bolletii, M. fortuitum, M. fortuitum* subsp. *Acetamidolyticum, M. boenickei, M. peregrinum, M porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. fallax, M. confluentis, M. flavescens, M. madagascariense, M. phlei, M. smegmatis, M goodii, M. wolinskyi, M. thermoresistibile, M. gadium, M. komossense, M. obuense, M. sphagni, M. agri, M. aichiense, M. alvei, M. arupense, M. brumae, M. canariasense, M chubuense, M. conceptionense, M. duvalii, M. elephantis, M. gilvum, M. hassiacum, M holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. pannense, M. phocaicum, M. poriferae, M. rhodesiae, M. seoulense*, or *M. tokaiense*.

In certain embodiments, the antigen is a mycolyl transferase or a fragment thereof. In certain embodiments, the antigen is a fragment of at least at least 10, 15, 20, 25, 50, 75, 100, 150, 200, or 250 amino acids of a gene product of a gene of the mycolyl transferase of a *mycobacterium* or a fragment thereof. In certain embodiments, the antigen is a fragment that can be identified using a variety of methods published for the prediction of antigenic determinants (see, e.g., Jameson B. A. and Wolf H., Comput Appl Biosci. 1988 March; 4(1):181-186; Pellequer J. L. and Westhof E., J Mol Graph. 1993 September; 11(3):204-10, 191-192; and Kolaskar A. S. and Tongaonkar P. C., FEBS Lett. 1990 Dec. 10; 276 (1-2):172-4). In certain more specific embodiments, the mycolyl transferase is *M. tuberculosis* Ag85A, *M. tuberculosis* Ag85B, or *M. tuberculosis* Ag85C or a fragment thereof.

In certain embodiments, the antigen is encoded by a gene of the esat-6 gene family. In certain embodiments, the antigen is a fragment of at least 10, 15, 20, 25, 50, 75, or at least 100 amino acids of a gene product of a gene of the esat-6 gene family or a fragment thereof. In certain embodiments, the antigen is a fragment that can be identified using a variety of methods published for the prediction of antigenic determinants (see, e.g., Jameson B. A. and Wolf H., Comput Appl Biosci. 1988 March; 4(1):181-186; Pellequer J. L. and Westhof E., J Mol Graph. 1993 September; 11(3):204-10, 191-192; and Kolaskar A. S. and Tongaonkar P. C., FEBS Lett. 1990 Dec. 10; 276 (1-2): 172-4).

In certain embodiments, the antigen is TB10.3, TB12.9, or TB10.4 or a fragment thereof belonging to the esat-6 gene family. In certain embodiments, the antigen is TB10.4, Ag85B, a fragment of TB10.4, or a fragment of Ag85B.

In certain embodiments, the antigen is a fusion protein between TB10.4 and Ag85B. In certain embodiments, the antigen is at least 10, 20, 30, 40, 50, 75, 100, 150, 200, 250, 300, 350, 400, 450, or at least 500 amino acids long. In certain embodiments, the antigen is encoded by a nucleic acid sequence that is 90%, 91%, 92%, 93%, 94%, 95%, 96%, 97%, 98%, 99%, or 100% identical to SEQ ID NO:4. In certain embodiments, the antigen comprises an amino acid sequence that is 90%, 91%, 92%, 93%, 94%, 95%, 96%, 97%, 98%, 99%, or 100% identical to SEQ ID NO:5.

In certain embodiments, the antigen described herein is fused to a signal peptide. Such signal peptides that can be fused to the antigens described herein include:

A signal peptide for targeting to the endoplasmic reticulum fused to a mycobacterial antigen; or A signal peptide for targeting to the endoplasmic reticulum fused to a mycolyl transferase of a *mycobacterium* or a fragment thereof; or A signal peptide for targeting to the endoplasmic reticulum fused to *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C; or A signal peptide for targeting to the endoplasmic reticulum fused to a gene product of a gene of the esat-6 gene family, or a fragment of at least 10, 15, 20, 25, 50, 75, or at least 100 amino acids of a gene product of a gene of the esat-6 gene family; or A signal peptide for targeting to the endoplasmic reticulum fused to (i) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C and (ii) a gene product of a gene of the esat-6 gene family, or a fragment of at least 10, 15, 20, 25, 50, 75, or at least 100 amino acids of a gene product of a gene of the esat-6 gene family; or In the following order from N-terminus to C-terminus a signal peptide for targeting to the endoplasmic reticulum fused to (i) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C and (ii) a gene product of a gene of the esat-6 gene family, or a fragment of at least 10, 15, 20, 25, 50, 75, or at least 100 amino acids of a gene product of a gene of the esat-6 gene family; or In the following order from N-terminus to C-terminus a signal peptide for targeting to the endoplasmic reticulum fused to (i) a gene product of a gene of the esat-6 gene family, or a fragment of at least 10, 15, 20, 25, 50, 75, or at least 100 amino acids of a gene product of a gene of the esat-6 gene family; and (ii) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C.

In certain embodiments, the antigen described herein is fused to an N-terminal signal peptide. In certain embodiments, a cleavage site is present between the antigen and the signal peptide. In certain more specific embodiments, protease cleavage between the signal peptide and the antigen results in free antigens with precise N-terminus (i.e., at least 50%, 60%, 70%, 80%, 90%, 95%, 98%, at least 99%, or 100% of the released antigen have the same N-terminal amino acid sequence). In certain embodiments, the N-terminal signal peptide directs targeting of the antigen described herein to the endoplasmic reticulum of the cell that is infected with the arenavirus. In certain embodiments, the N-terminal signal peptide that directs targeting of the antigen to the endoplasmic reticulum includes, but is not limited to, the signal peptide of nerve growth factor, midkine, LAMP1, LIMPII, endotubin or negative factor gene (Nef) (see, e.g., Ladunga I., Curr Opin Biotechnol. 2000 February; 11(1):13-8).

In certain embodiments, the signal peptide that is fused to the antigen described herein is a tissue plasminogen activator (tPA). In certain embodiments, the tPA signal peptide for use with the present invention is encoded by a nucleic acid sequence that aligns with at least 5, 10, 15, 20, 25, 30, 35, 40, 45, 50, 60, or at least 70 nucleic acids of SEQ ID NO:6 as determined over the entire length of the tPA signal peptide nucleic acid sequence using BLAST alignment software. In certain embodiments, the signal peptide for use with the present invention comprises an amino acid sequence that aligns with at least 3, 6, 9, 12, 15, 18, 21, or at least 24 amino acids of SEQ ID NO:7 as determined over the entire length of the signal peptide using BLAST alignment software.

In certain embodiments, the signal peptide-antigen fusion for use with the present invention is at least 10, 20, 30, 40, 50, 75, 100, 150, 200, 250, 300, 350, 400, 450, or at least 500 amino acids long. In certain embodiments, the signal peptide-antigen fusion is encoded by a nucleic acid sequence that is 90%, 91%, 92%, 93%, 94%, 95%, 96%, 97%, 98%, 99%, or 100% identical to SEQ ID NO:2. In certain embodiments, the signal peptide-antigen fusion comprises an amino acid sequence that is 90%, 91%, 92%, 93%, 94%, 95%, 96%, 97%, 98%, 99%, or 100% identical to SEQ ID NO:3.

Nucleic acid sequences encoding a mycobacterial antigen can be introduced in the genome of an infectious, replication-deficient arenavirus by substitution of the nucleic acid sequence of the open reading frame (ORF) of glycoprotein GP, the matrix protein Z, the nucleoprotein NP, or the polymerase protein L. In other embodiments, the nucleic acid sequence encoding the mycobacterial antigen is fused to the open reading frame (ORF) of glycoprotein GP, the matrix protein Z, the nucleoprotein NP, or the polymerase protein L. The nucleotide sequence encoding the mycobacterial antigen, once inserted into the genome of an infectious, replication-deficient arenavirus, can be transcribed and/or expressed under control of the four arenavirus promoters (5' UTR and 3' UTR of the S segment, and 5' UTR and 3' UTR of the L segment), as well as ribonucleic acids that can be inserted with regulatory elements that can be read by the viral RNA-dependent RNA polymerase, cellular RNA polymerase I, RNA polymerase II or RNA polymerase III, such as duplications of viral promoter sequences that are naturally found in the viral UTRs, the 28S ribosomal RNA promoter, the beta-actin promoter or the 5S ribosomal RNA promoter, respectively. The nucleic acids encoding the mycobacterial antigen can be transcribed and/or expressed either by themselves or as read-through by fusion to arenavirus open reading frames and genes, respectively, and/or in combination with one or more, e.g., two, three or four, internal ribosome entry sites.

In one embodiment of the invention, the antigen is one that is useful for the prevention of infectious disease. In a specific embodiment, antigens is derived from *Mycobacterium tuberculosis*.

In one embodiment, open reading frame that encodes the glycoprotein of the arenavirus is substituted by nucleic acid sequences encoding a mycobacterial antigen. In certain embodiments, the open reading frame that encodes the glycoprotein of the arenavirus is substituted by nucleic acid sequences encoding antigen that is a fragment of at least at least 10, 15, 20, 25, 50, 75, 100, 150, 200, or 250 amino acids of a gene product of a gene of the mycolyl transferase of a *mycobacterium* or a fragment thereof. In certain embodiments, the antigen is a fragment of at least 10, 15, 20, 25, 50, 75, or at least 100 amino acids of a gene product of a gene of the esat-6 gene family or a fragment thereof. In certain embodiments, the antigen fragment can be identified using a variety of methods published for the prediction of antigenic determinants (see, e.g., Jameson B. A. and Wolf H., Comput Appl Biosci. 1988 March; 4(1):181-186; Pellequer J. L. and Westhof E., J Mol Graph. 1993 September; 11(3):204-10, 191-192; and Kolaskar A. S. and Tongaonkar P. C., FEBS Lett. 1990 Dec. 10; 276 (1-2):172-4).

In certain embodiments, the open reading frame that encodes the glycoprotein of the arenavirus is substituted by nucleic acid sequences encoding antigens including, but not limited to, TB10.4, Ag85B, a fragment of TB10.4, or a fragment of Ag85B.

In certain embodiments, the open reading frame that encodes the glycoprotein of the arenavirus is substituted by nucleic acid sequences encoding an antigen that is a fusion protein between TB10.4 and Ag85B. In certain embodiments, the open reading frame that encodes the glycoprotein of the arenavirus is substituted by nucleic acid sequences encoding an antigen that is at least 10, 20, 30, 40, 50, 75, 100, 150, 200, 250, 300, 350, 400, 450, or at least 500 amino acids long. In certain embodiments, the open reading frame that encodes the glycoprotein of the arenavirus is substituted by nucleic acid sequence that is 90%, 91%, 92%, 93%, 94%, 95%, 96%, 97%, 98%, 99%, or 100% identical to SEQ ID NO:4. In certain embodiments, the open reading frame that encodes the glycoprotein of the arenavirus is substituted by nucleic acid sequence that encodes for an amino acid that is 90%, 91%, 92%, 93%, 94%, 95%, 96%, 97%, 98%, 99%, or 100% identical to SEQ ID NO:5.

In certain embodiments, the open reading frame that encodes the glycoprotein of the arenavirus is substituted by nucleic acid sequences encoding an antigen that is fused to an N-terminal signal peptide to direct targeting of the antigen described herein to the endoplasmic reticulum of the cell that is infected with the arenavirus. In certain embodiments, the open reading frame that encodes the glycoprotein of the arenavirus is substituted by a signal peptide-antigen fusion that is at least 10, 20, 30, 40, 50, 75, 100, 150, 200, 250, 300, 350, 400, 450, or at least 500 amino acids long. In certain embodiments, the open reading frame that encodes the glycoprotein of the arenavirus is substituted by nucleic acid sequence that is 90%, 91%, 92%, 93%, 94%, 95%, 96%, 97%, 98%, 99%, or 100% identical to SEQ ID NO:2. In certain embodiments, the open reading frame that encodes the glycoprotein of the arenavirus is substituted by nucleic acid sequence that encodes for an amino acid that is 90%, 91%, 92%, 93%, 94%, 95%, 96%, 97%, 98%, 99%, or 100% identical to SEQ ID NO:3.

6.3 Generation of Infectious, Replication-Deficient Arenavirus Expressing a Mycobacterial Antigen Generally, arenavirus particles can be recombinantly produced by standard reverse genetic techniques as described for LCMV (L. Flatz, A. Bergthaler, J. C. de la Torre, and D. D. Pinschewer, Proc Natl Acad Sci USA 103:4663-4668, 2006; A. B. Sanchez and J. C. de la Torre, Virology 350:370, 2006; E. Ortiz-Riano, B. Y. Cheng, J. C. de la Torre, L. Martinez-Sobrido. J Gen Virol. 2013 Jan. 30. Epub ahead of print). To generate infectious, replication-deficient arenaviruses for use with the present invention these techniques can be used, however, the genome of the rescued virus is modified as described in Section 6.1. These modifications can be: i) one or more, e.g., two, three or four, of the four arenavirus open reading frames (glycoprotein (GP); nucleoprotein (NP); the matrix protein Z; the RNA-dependent RNA polymerase L) are removed or is functionally inactivated to prevent formation of infectious particles in normal cells albeit still allowing gene expression in arenavirus vector-infected host cells; and ii) a nucleic acids coding for mycobacterial antigens can be introduced. Infectious, replication-deficient viruses as described herein can be produced as described in International Patent Application Publication No. WO 2009/083210 (application number PCT/EP2008/010994), which is incorporated by reference herein in its entirety.

Once generated from cDNA, the infectious, replication-deficient arenaviruses provided herein can be propagated in complementing cells. Complementing cells are cells that provide the functionality that has been eliminated from the replication-deficient arenavirus by modification of its genome (e.g., if the open reading frame encoding the GP protein is deleted or functionally inactivated, a complementing cell does provide the GP protein).

Owing to the removal or functional inactivation of one or more of the viral genes in arenavirus vectors (here deletion of the glycoprotein, GP, will be taken as an example), arenavirus vectors can be generated and expanded in cells providing in trans the deleted viral gene(s), e.g., the GP in the present example. Such a complementing cell line, henceforth referred to as C-cells, is generated by transfecting a mammalian cell line such as BHK-21, HEK293, VERO or other (here BHK-21 will be taken as an example) with one or more plasmid(s) for expression of the viral gene(s) of interest (complementation plasmid, referred to as C-plasmid). The C-plasmid(s) express the viral gene(s) deleted in the arenavirus vector to be generated under control of one or more expression cassettes suitable for expression in mammalian cells, e.g., a mammalian polymerase II promoter such as the CMV or EF1alpha promoter with a polyadenylation signal. In addition, the complementation plasmid features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in E. coli, the plasmid additionally features a bacterial selection marker, such as an ampicillin resistance cassette.

The cells to be used, e.g., BHK-21, HEK293, MC57G or other, are kept in culture and are transfected with the complementation plasmid(s) using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing C-cell clones are identified using Western blot or flow cytometry procedures with antibodies directed against the viral protein(s) of interest. As an alternative to the use of stably transfected C-cells transient transfection of normal cells can complement the missing viral gene(s) in each of the steps where C-cells will be used below.

Plasmids needed are of two types: i) Two plasmids, referred to as TF-plasmids for expressing intracellularly in C-cells the minimal transacting factors of the arenavirus, is derived from e.g., NP and L proteins of LCMV in the present example; and ii) Plasmids, referred to as GS-plasmids, for expressing intracellularly in C-cells the arenavirus vector genome segments, e.g., the segments with designed modifications. TF-plasmids express the NP and L proteins of the respective arenavirus vector under control of an expression cassette suitable for protein expression in mammalian cells, typically e.g., a mammalian polymerase II promoter such as the CMV or EF1alpha promoter, either one of them preferentially in combination with a polyadenylation signal. GS-plasmids express the small (S) and the large (L) genome segments of the vector. Typically, polymerase I-driven expression cassettes or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing T7, or C-cells are constructed to additionally express T7 in a stable manner.

For recovering of the arenavirus vector, the following procedures are envisaged. First day: C-cells, typically 80% confluent in M6-well plates, are transfected with a mixture of the two TF-plasmids plus the two GS-plasmids. For this one can exploit any of the commonly used strategies such as calcium-phosphate, liposome-based protocols or electroporation.

3-5 days later: The culture supernatant (arenavirus vector preparation) is harvested, aliquoted and stored at 4° C., −20° C. or −80° C. depending on how long the arenavirus vector should be stored prior to use. Then the arenavirus vector preparation's infectious titer is assessed by an immunofocus assay on C-cells.

The invention furthermore relates to expression of a mycobacterial antigen in a cell culture wherein the cell culture is infected with an infectious, replication-deficient arenavirus expressing a mycobacterial antigen. When used for expression of a mycobacterial antigen in cultured cells, the following two procedures are envisaged:

i) The cell type of interest is infected with the arenavirus vector preparation described herein at a multiplicity of infection (MOI) of one or more, e.g., two, three or four, resulting in production of the mycobacterial antigen in all cells already shortly after infection.

ii) Alternatively, a lower MOI can be used and individual cell clones can be selected for their level of virally driven mycobacterial antigen expression. Subsequently individual clones can be expanded infinitely owing to the non-cytolytic nature of arenavirus vectors. Irrespective of the approach, the mycobacterial antigen can subsequently be collected (and purified) either from the culture supernatant or from the cells themselves, depending on the properties of the mycobacterial antigen produced. However, the invention is not limited to these two strategies, and other ways of driving expression of mycobacterial antigen using infectious, replication-deficient arenaviruses as vectors may be considered.

6.4 Nucleic Acids, Vector Systems and Cell Lines

In one embodiment, described herein is a nucleic acid sequence encoding the large genomic segment (L segment) of an infectious, replication-deficient arenavirus described herein, in which one open reading frame of the genomic segment is deleted or functionally inactivated, and the genomic segment comprises a nucleotide sequence encoding a mycobacterial antigen.

In one embodiment, described herein is a nucleic acid sequence that encodes the short genomic segment (S segment) of an infectious, replication-deficient arenavirus described herein, in which one open reading frame of the genomic segment is deleted or functionally inactivated and wherein the short genomic segment comprises a nucleotide sequence encoding a mycobacterial antigen. In another embodiment, described herein is a nucleic acid sequence that encodes the short genomic segment (S segment) of an infectious, replication-deficient arenavirus described herein, in which the open reading frame of the glycoprotein gene is deleted or functionally inactivated and wherein the short genomic segment comprises a nucleotide sequence encoding a mycobacterial antigen.

In a more specific embodiment, provided herein is a nucleic acid encoding an arenavirus genomic segment comprising a sequence that is at least 90%, 91%, 92%, 93%, 94%, 95%, 96%, 97%, 98%, at least 99%, or 100% identical to the sequence of SEQ ID NO:1. In another embodiment, provided herein is a nucleic acid that encodes an arenavirus genomic segment comprising (i) a nucleotide sequence that is at least 90%, 91%, 92%, 93%, 94%, 95%, 96%, 97%, 98%, at least 99%, or 100% identical to the sequence of nucleotide 1639 to 3315 of SEQ ID NO:11; and (ii) a nucleotide sequence encoding a mycobacterial antigen. In another embodiment, provided herein is a nucleic acid that encodes an arenavirus genomic segment comprising (i) a nucleotide sequence that is at least 90%, 91%, 92%, 93%, 94%, 95%, 96%, 97%, 98%, at least 99%, or 100% identical to the sequence of nucleotide 1639 to 3315 of SEQ ID NO:11; and (ii) a nucleotide sequence encoding a mycobacterial antigen fused to a signal peptide that targets the mycobacterial antigen to the endoplasmic reticulum.

In another embodiment, provided herein is a nucleic acid that encodes an arenavirus genomic segment comprising (i) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1639 to 3315 of SEQ ID NO:11; and (ii) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1639 to 3315 of SEQ ID NO:11; and (ii) a nucleotide sequence encoding a mycobacterial antigen fused to a signal peptide that targets the mycobacterial antigen to the endoplasmic reticulum.

In another embodiment, provided herein is a nucleic acid that encodes an arenavirus genomic segment comprising (i) a nucleotide sequence that is at least 90%, 91%, 92%, 93%, 94%, 95%, 96%, 97%, 98%, at least 99%, or 100% identical to the sequence of nucleotide 1640 to 3316 of SEQ ID NO:12; and (ii) a nucleotide sequence encoding a mycobacterial antigen. In another embodiment, provided herein is a nucleic acid that encodes an arenavirus genomic segment comprising (i) a nucleotide sequence with that is at least 90%, 91%, 92%, 93%, 94%, 95%, 96%, 97%, 98%, at least 99%, or 100% identical to the sequence of nucleotide 1640 to 3316 of SEQ ID NO:12; and (ii) a nucleotide sequence encoding a mycobacterial antigen fused to a signal peptide that targets the mycobacterial antigen to the endoplasmic reticulum.

In another embodiment, provided herein is a nucleic acid that encodes an arenavirus genomic segment comprising (i) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1640 to 3316 of SEQ ID NO:12; and (ii) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1640 to 3316 of SEQ ID NO:12; and (ii) a nucleotide sequence encoding a mycobacterial antigen fused to a signal peptide that targets the mycobacterial antigen to the endoplasmic reticulum.

In one embodiment, described herein is a vector system comprising one or more vectors that together encode the genome of an infectious, replication-deficient arenavirus particle described herein. Specifically, provided herein is a vector system wherein the one or more vectors encode two arenavirus genomic segments, namely an L segment and an S segment, of an infectious, replication-deficient arenavirus described herein. Such a vector system can encode (on one or more separate DNA molecules):

- An arenavirus S genomic segment that is modified such that an arenavirus particle carrying this modified S genomic segment cannot produce infectious progeny virus particles and an arenavirus L genomic segment that comprises a nucleotide sequence encoding (in sense or antisense) a mycobacterial antigen;
- An arenavirus L genomic segment that is modified such that an arenavirus particle carrying this modified L genomic segment cannot produce infectious progeny virus particles and an arenavirus S genomic segment that comprises a nucleotide sequence encoding (in sense or antisense) a mycobacterial antigen;
- An arenavirus S genomic segment that is modified such that an arenavirus particle carrying this modified S genomic segment cannot produce infectious progeny virus particles and wherein the arenavirus S genomic segment comprises a nucleotide sequence encoding (in sense or antisense) a mycobacterial antigen and a wild type arenavirus L genomic segment; or
- An arenavirus L genomic segment that is modified such that an arenavirus particle carrying this modified L genomic segment cannot produce infectious progeny virus particles and wherein the arenavirus L genomic segment comprises a nucleotide sequence encoding (in sense or antisense) a mycobacterial antigen and a wild type arenavirus S genomic segment.

In certain embodiments, described herein is a nucleic acid sequence encoding an arenavirus (e.g., LCMV) genomic segment in which the open reading frame encoding the GP of the S genomic segment is substituted with a nucleotide sequence encoding:

- A signal peptide for targeting to the endoplasmic reticulum fused to a mycobacterial antigen; or
- A signal peptide for targeting to the endoplasmic reticulum fused to a mycolyl transferase of a *mycobacterium* or a fragment thereof; or
- A signal peptide for targeting to the endoplasmic reticulum fused to *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C; or
- A signal peptide for targeting to the endoplasmic reticulum fused to a gene product of a gene of the esat-6 gene family, or a fragment of at least 10, 15, 20, 25, 50, 75, or at least 100 amino acids of a gene product of a gene of the esat-6 gene family; or
- A signal peptide for targeting to the endoplasmic reticulum fused to (i) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C and (ii) a gene product of a gene of the esat-6 gene family, or a fragment of at least 10, 15, 20, 25, 50, 75, or at least 100 amino acids of a gene product of a gene of the esat-6 gene family; or
- In the following order from N-terminus to C-terminus: a signal peptide for targeting to the endoplasmic reticulum fused to (i) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C and (ii) a gene product of a gene of the esat-6 gene family, or a fragment of at least 10, 15, 20, 25, 50, 75, or at least 100 amino acids of a gene product of a gene of the esat-6 gene family; or
- In the following order from N-terminus to C-terminus: a signal peptide for targeting to the endoplasmic reticulum fused to (i) a gene product of a gene of the esat-6 gene family, or a fragment of at least 10, 15, 20, 25, 50, 75, or at least 100 amino acids of a gene product of a gene of the esat-6 gene family; and (ii) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C.

In another embodiment, provided herein is a cell wherein the cell comprises a nucleic acid or a vector system described above in this section. Cell lines derived from such cells, cultures comprising such cells, and methods of culturing such cells infected are also provided herein.

6.5 Methods of Use

In one embodiment, provided herein are methods of treating an infection in a subject comprising administering to the subject an infectious, replication-deficient arenavirus expressing a mycobacterial antigen as described herein. In a specific embodiment, a method for treating an infection described herein comprises administering to a subject in need thereof an effective amount of an infectious, replication-deficient arenavirus expressing a mycobacterial antigen described herein or a composition thereof. The subject can be a mammal, a mouse, a rat, a domesticated animal, such as, but not limited to, a cow, a horse, a sheep, a pig, a goat, a cat, a dog, a hamster, a donkey. In a specific embodiment, the subject is a human.

In another embodiment, provided herein are methods for inducing an immune response against a *mycobacterium* in a subject comprising administering to the subject an infectious, replication-deficient arenavirus expressing a mycobacterial antigen or a composition thereof.

In another embodiment, the subjects to whom an infectious, replication-deficient arenavirus expressing a mycobacterial antigen described herein or a composition thereof is administered have, are susceptible to, or are at risk for a mycobacterial infection. In another specific embodiment, the subjects to whom an infectious, replication-deficient arenavirus expressing a mycobacterial antigen described herein or a composition thereof is administered are infected with, are susceptible to, or are at risk for, an infection with *mycobacterium*. In a specific embodiment, the subjects to whom an infectious, replication-deficient arenavirus expressing a mycobacterial antigen described herein or a composition thereof is administered are infected with, susceptible to, or are at risk for, an infection with *Mycobacterium tuberculosis*.

In another embodiment, the subjects to whom an infectious, replication-deficient arenavirus expressing a mycobacterial antigen described herein or a composition thereof is administered are suffering from, are susceptible to, or are at risk for, an infection with *Mycobacterium tuberculosis* in the pulmonary system, central nervous system, lymphatic system, gastrointestinal system, or circulatory system among others. In a specific embodiment, the subjects to whom an infectious, replication-deficient arenavirus expressing a mycobacterial antigen described herein or a composition thereof is administered are suffering from, are susceptible to, or are at risk for, an infection with *Mycobacterium tuberculosis* in one or more organs of the body, including but not limited to the brain, kidneys, bone, bone marrow, uterus, testicles, uterus, or lungs. In a more specific embodiment, the subjects to whom an infectious, replication-deficient arenavirus expressing a mycobacterial antigen described herein or a composition thereof is administered are suffering from, are susceptible to, or are at risk for, a pulmonary tuberculosis infection with *Mycobacterium tuberculosis* in the lungs.

In another embodiment, the subjects to whom an infectious, replication-deficient arenavirus expressing a mycobacterial antigen described herein or a composition thereof is administered to a subject suffering from symptoms including but not limited to unexplained weight loss, tiredness, fatigue, shortness of breath, fever, night sweats, chills, and a loss of appetite, persistent cough, coughing up blood or sputum, chest pain, or pain with breathing or coughing among others.

In another embodiment, an infectious, replication-deficient arenavirus expressing a mycobacterial antigen as described herein or a composition thereof is administered to a subject of any age group suffering from, are susceptible to, or are at risk for, an infection with *Mycobacterium tuberculosis*. In a specific embodiment, an infectious, replication-deficient arenavirus expressing a mycobacterial antigen as described herein or a composition thereof is administered to a subject with a compromised immune system, a subject suffering from malnutrition or diabetes, a subject who uses tobacco, a child, or a young adult who is suffering from, are susceptible to, or are at risk for, an infection with *Myco-* bacterium tuberculosis. In a more specific embodiment, an infectious, replication-deficient arenavirus expressing a mycobacterial antigen as described herein or a composition thereof is administered to a subject with a compromised immune system due to HIV infection, who is suffering from, is susceptible to, or is at risk for, an infection with *Mycobacterium tuberculosis*. In yet another specific embodiment, an infectious, replication-deficient arenavirus expressing a mycobacterial antigen as described herein or a composition thereof is administered to a subject who is a child of 0, 1, 2, 3, 4, 5, 6, 7, 8, 9, 10, 11, 12, 13, 14, or 15 years of age suffering from, are susceptible to, or are at risk for, an infection with *Mycobacterium tuberculosis*. In yet another specific embodiment, an infectious, replication-deficient arenavirus expressing a mycobacterial antigen described herein or a composition thereof is administered to a subject who is an infant suffering from, is susceptible to, or is at risk for, an infection with *Mycobacterium tuberculosis*. In yet another specific embodiment, an infectious, replication-deficient arenavirus expressing a mycobacterial antigen described herein or a composition thereof is administered to a subject who is an infant of 0, 1, 2, 3, 4, 5, 6, 7, 8, 9, 10, 11, or 12 months of age suffering from, is susceptible to, or is at risk for, an infection with *Mycobacterium tuberculosis*.

In another embodiment, an infectious, replication-deficient arenavirus expressing a mycobacterial antigen described herein or a composition thereof is administered to subjects with a heightened risk of disseminated *Mycobacterium tuberculosis* infection. In a specific embodiment, an infectious, replication-deficient arenavirus expressing a mycobacterial antigen described herein or a composition thereof is administered to subjects in neonatal period with immature neonatal immune system.

In another embodiment, an infectious, replication-deficient arenavirus expressing a mycobacterial antigen as described herein or a composition thereof is administered to a subject having a latent or 'sleeping' infection with *Mycobacterium tuberculosis*. In a specific embodiment, an infectious, replication-deficient arenavirus expressing a mycobacterial antigen described herein or a composition thereof is administered to a subject having a latent or 'sleeping' infection with *Mycobacterium tuberculosis*, which is not contagious, but can still develop into TB later in life.

In another embodiment, administering an infectious, replication-deficient arenavirus expressing a mycobacterial antigen as described herein or a composition thereof to subjects confer cell-mediated immunity (CMI) against an infection with *Mycobacterium tuberculosis*. Without being bound by theory, in another embodiment, an infectious, replication-deficient arenavirus expressing a mycobacterial antigen as described herein or a composition thereof infects and expresses antigens of interest in antigen presenting cells (APC) of the host (e.g., macrophages) for direct presentation of antigens on Major Histocompatibility Complex (MHC) class I and II. In another embodiment, administering an infectious, replication-deficient arenavirus expressing a mycobacterial antigen described herein or a composition thereof to subjects induce plurifunctional IFN-γ and TNF-α co-producing Mtb-specific CD4+ and CD8+ T cell responses (IFN-γ is produced by CD4+ and CD8+ T cells and TNF-α is produced by CD4+ T cells) of high magnitude to treat or prevent an infection with *Mycobacterium tuberculosis*.

In another embodiment, administering an infectious, replication-deficient arenavirus expressing a mycobacterial antigen or a composition thereof reduces the risk that an individual will develop an infection with *Mycobacterium tuberculosis* by at least about 10%, at least about 20%, at least about 25%, at least about 30%, at least about 35%, at least about 40%, at least about 50%, at least about 60%, at least about 70%, at least about 80%, at least about 90%, or more, compared to the risk of developing an infection with *Mycobacterium tuberculosis* in the absence such treatment.

In another embodiment, administering an infectious, replication-deficient arenavirus expressing a mycobacterial antigen or a composition thereof reduces the symptoms of an infection with *Mycobacterium tuberculosis* by at least about 10%, at least about 20%, at least about 25%, at least about 30%, at least about 35%, at least about 40%, at least about 50%, at least about 60%, at least about 70%, at least about 80%, at least about 90%, or more, compared to the manifestation of the symptoms of an infection with *Mycobacterium tuberculosis* in the absence such treatment.

In another embodiment, administering an infectious, replication-deficient arenavirus expressing a mycobacterial antigen or a composition thereof in subjects with immature neonatal immune system induces cell-mediated immunity (CMI) response against an infection with *Mycobacterium tuberculosis* by at least about 10%, at least about 20%, at least about 25%, at least about 30%, at least about 35%, at least about 40%, at least about 50%, at least about 60%, at least about 70%, at least about 80%, at least about 90%, or more, compared to cell-mediated immunity (CMI) response against an infection with *Mycobacterium tuberculosis* in the absence such treatment.

Changes in cell-mediated immunity (CMI) response function against an infection with *Mycobacterium tuberculosis* induced by administering an infectious, replication-deficient arenavirus expressing a mycobacterial antigen or a composition thereof in subjects can be measured by any assay known to the skilled artisan including, but not limited to flow cytometry (see, e.g., Perfetto S. P. et al., Nat Rev Immun. 2004; 4(8):648-55), lymphocyte proliferation assays (see, e.g., Bonilla F. A. et al., Ann Allergy Asthma Immunol. 2008; 101:101-4; and Hicks M. J. et al., Am J Clin Pathol. 1983; 80:159-63), assays to measure lymphocyte activation including determining changes in surface marker expression following activation of measurement of cytokines of T lymphocytes (see, e.g., Caruso A. et al., Cytometry. 1997; 27:71-6), ELISPOT assays (see, e.g., Czerkinsky C. C. et al., J Immunol Methods. 1983; 65:109-121; and Hutchings P. R. Et al., J Immunol Methods. 1989; 120:1-8), or Natural killer cell cytotoxicity assays (see, e.g., Bonilla F. A. et al., Ann Allergy Asthma Immunol. 2005 May; 94 (5 Suppl 1):S1-63).

In another embodiment, described herein is a method of use with an infectious, replication-deficient arenavirus (e.g., LCMV) expressing a mycobacterial antigen as described herein in which the open reading frame encoding the GP of the S genomic segment is substituted with a nucleotide sequence encoding:

A signal peptide for targeting to the endoplasmic reticulum fused to a mycobacterial antigen; or A signal peptide for targeting to the endoplasmic reticulum fused to a mycolyl transferase of a *mycobacterium* or a fragment thereof; or A signal peptide for targeting to the endoplasmic reticulum fused to *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C; or A signal peptide for targeting to the endoplasmic reticulum fused to a gene product of a gene of the esat-6 gene family, or a fragment of at least 10, 15, 20, 25, 50, 75, or at least 100 amino acids of a gene product of a gene of the esat-6 gene family; or A signal peptide for targeting to the endoplasmic reticulum fused to (i) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C and (ii) a gene product of a gene of the esat-6 gene family, or a fragment of at least 10, 15, 20, 25, 50, 75, or at least 100 amino acids of a gene product of a gene of the esat-6 gene family; or In the following order from N-terminus to C-terminus: a signal peptide for targeting to the endoplasmic reticulum fused to (i) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C and (ii) a gene product of a gene of the esat-6 gene family, or a fragment of at least 10, 15, 20, 25, 50, 75, or at least 100 amino acids of a gene product of a gene of the esat-6 gene family; or In the following order from N-terminus to C-terminus: a signal peptide for targeting to the endoplasmic reticulum fused to (i) a gene product of a gene of the esat-6 gene family, or a fragment of at least 10, 15, 20, 25, 50, 75, or at least 100 amino acids of a gene product of a gene of the esat-6 gene family; and (ii) *M. tuberculosis* Ag85A, *M. tuberculosis* Ag85B, or *M. tuberculosis* Ag85C, or a fragment of at least 10, 15, 20, 25, 50, 75, 100, 150, 200, or 250 amino acids of *M. tuberculosis* Ag85A, *M. tuberculosis* Ag85B, or *M. tuberculosis* Ag85C.

6.6 Compositions, Administration and Dosage

The invention furthermore relates to vaccines, immunogenic compositions, and pharmaceutical compositions comprising a genetically engineered arenavirus as described herein. Such vaccines and pharmaceutical compositions can be formulated according to standard procedures in the art.

In another embodiment, provided herein are compositions comprising an infectious, replication-deficient arenaviruses described herein. Such compositions can be used in methods of treatment and prevention of disease. In a specific embodiment, the compositions described herein are used in the treatment of subjects infected with, or are susceptible to, an infection with *Mycobacterium tuberculosis*. In another specific embodiment, the immunogenic compositions provided herein can be used to induce an immune response in a host to whom the composition is administered. The immunogenic compositions described herein can be used as vaccines and can accordingly be formulated as pharmaceutical compositions. In a specific embodiment, the immunogenic compositions described herein are used in the prevention of infection of subjects (e.g., human subjects) by *Mycobacterium tuberculosis*.

In certain embodiments, the compositions described herein (e.g., the immunogenic compositions) comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a infectious, replication-deficient arenavirus particle, but when the compound is administered alone does not generate an immune response to the infectious, replication-deficient arenavirus particle. In some embodiments, the adjuvant generates an immune response to the infectious, replication-deficient arenavirus particle and does not produce an allergy or other adverse reaction. Adjuvants can enhance an immune response by several mechanisms including, e.g., lymphocyte recruitment, stimulation of B and/or T cells, and stimulation of macrophages. When a vaccine or immunogenic composition of the invention comprises adjuvants or is administered together with one or more adjuvants, the adjuvants that can be used include, but are not limited to, mineral salt adjuvants or mineral salt gel adjuvants, particulate adjuvants, microparticulate adjuvants, mucosal adjuvants, and immunostimulatory adjuvants. Examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), ASO4 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)).

The compositions comprise the infectious, replication-deficient arenaviruses described herein alone or, preferably, together with a pharmaceutically acceptable carrier. Suspensions or dispersions of genetically engineered arenaviruses, especially isotonic aqueous suspensions or dispersions, can be used. The pharmaceutical compositions may be sterilized and/or may comprise excipients, e.g., preservatives, stabilizers, wetting agents and/or emulsifiers, solubilizers, salts for regulating osmotic pressure and/or buffers and are prepared in a manner known per se, for example by means of conventional dispersing and suspending processes. The said dispersions or suspensions may comprise viscosity-regulating agents. The suspensions or dispersions are kept at temperatures around 2-4° C., or preferentially for longer storage may be frozen and then thawed shortly before use. For injection, the vaccine or immunogenic preparations may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

In certain embodiments, the compositions described herein additionally comprise a preservative, e.g., the mercury derivative thimerosal. In a specific embodiment, the pharmaceutical compositions described herein comprises 0.001% to 0.01% thimerosal. In other embodiments, the pharmaceutical compositions described herein do not comprise a preservative.

The pharmaceutical compositions comprise from about $10^3$ to about $10^{11}$ focus forming units of the genetically engineered arenaviruses. Unit dose forms for parenteral administration are, for example, ampoules or vials, e.g., vials containing from about $10^3$ to $10^{10}$ focus forming units or $10^5$ to $10^{15}$ physical particles of genetically engineered arenaviruses.

In another embodiment, a vaccine or immunogenic composition provided herein is administered to a subject by, including but not limited to, oral, intradermal, intramuscular, intraperitoneal, intravenous, subcutaneous, percutaneous, intranasal and inhalation routes, and via scarification (scratching through the top layers of skin, e.g., using a bifurcated needle). Specifically, subcutaneous or intravenous routes can be used.

For administration intranasally or by inhalation, the preparation for use according to the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflators may be formulated containing a powder mix of the compound and a suitable powder base such as lactose or starch.

The dosage of the active ingredient depends upon the type of vaccination and upon the subject, and their age, weight, individual condition, the individual pharmacokinetic data, and the mode of administration.

The invention relates also to processes and to the use of genetically engineered arenaviruses for the manufacture of vaccines in the form of pharmaceutical preparations, which comprise genetically engineered arenaviruses as active ingredient. The pharmaceutical compositions of the present invention are prepared in a manner known per se, for example by means of conventional mixing and/or dispersing processes.

6.7 Assays (a) MHC-Peptide Multimer Staining Assay for Detection of Antigen-Specific CD8+ T-Cell Proliferation Any assay known to the skilled artisan can be used to test antigen-specific CD8+ T-cell responses. For example, the MHC-peptide tetramer staining assay can be used (see, e.g., Altman J. D. et al., Science. 1996; 274:94-96; and Murali-Krishna K. et al., Immunity 1998; 8:177-187). Briefly, the assay comprises the following steps, a tetramer assay is used to detect the presence of antigen specific T-cells. In order for a T-cell to detect the peptide to which it is specific, it must both recognize the peptide and the tetramer of MHC molecules custom made for an antigen specific T-cell (typically fluorescently labeled). The tetramer is then detected by flow cytometry via the fluorescent label.

(b) ELISPOT Assay for Detection of Antigen-Specific CD4+ T-Cell Proliferation

Any assay known to the skilled artisan can be used to test antigen-specific CD4+ T-cell responses. For example, the ELISPOT assay can be used (see, e.g., Czerkinsky C. C. et al., J Immunol Methods. 1983; 65:109-121; and Hutchings P. R. Et al., J Immunol Methods. 1989; 120:1-8). Briefly, the assay comprises the following steps: An immunospot plate is coated with an anti-cytokine antibody. Cells are incubated in the immunospot plate. Cells secrete cytokines and are then washed off. Plates are then coated with a second biotyinlated-anticytokine antibody and visualized with an avidin-HRP system.

(c) Intracellular Cytokine Assay for Detection of Functionality of CD8+ and CD4+ T-Cell Responses Any assay known to the skilled artisan can be used to test the functionality of CD8+ and CD4+ T cell responses. For example, the intracellular cytokine assay combined with flow cytometry can be used (see, e.g., Suni M. A. et al., J Immunol Methods. 1998; 212:89-98; Nomura L. E. et al., Cytometry. 2000; 40:60-68; and Ghanekar S. A. et al., Clinical and Diagnostic Laboratory Immunology. 2001; 8:628-63). Briefly, the assay comprises the following steps: activation of cells via a specific peptide, an inhibition of protein transport (e.g., brefeldin A) is added to retain the cytokines within the cell. After washing, antibodies to other cellular markers can be added to the cells. Cells are then fixed and permeabilized. The anti-cytokine antibody is added and the cells can be analyzed by flow cytometry. Various publications, patents and patent applications are cited herein, the disclosures of which are incorporated by reference in their entireties.

(d) Assay for Measuring Arenavirus Vector Infectivity

Any assay known to the skilled artisan can be used for measuring the infectivity of an arenavirus vector preparation. For example, a typical immunofocus assay with complementing cells (C-cells) following commonly are used for this purpose. C-cell monolayers, typically in M24 well plates, 80% confluent, are infected with 10-fold dilutions of the arenavirus vector preparation for 90 min Subsequently, the cell layer is overlayed with suitable cell culture medium supplemented with 1% methylcellulose. Two to three days later, depending on the permissiveness of the C-cell line used, the culture supernatant is removed, the cell layer is fixed, typically with ethanol/acetone or with formalin 4%, followed by permeabilization of the cell layer using mild detergents. Subsequently, arenavirus-vector-infected cell foci are identified using mono- or polyclonal antibody preparation(s) against one of the proteins in the arenavirus vector to be tested or against the antigen introduced. Bound antibody is detected using appropriate reagents, such as anti-isotype or anti-species antibodies that are conjugated to a system for visualization such as horse radish peroxidase, followed by a color reaction with suitable chromogens such as o-phenylenediamine. The resulting spots on the plate are counted to calculate the number of infectious focus forming units (FFU) per volume of arenavirus vector preparation (see, e.g., Flint, S. J.; Enquist, W., Racaniello, V. R., and Skalka, A. M. (2009). "Virological Methods". Principles of Virology. ASM Press. ISBN 1-55581-443-3).

(e) Assay for Confirming Replication-Deficiency of Viral Vectors

Any assay known to the skilled artisan that determines concentration of infectious and replication-competent virus particles can also be used as a to measure replication-deficient viral particles in a sample. For example, a typical immunofocus assay with non-complementing cells following commonly are used for this purpose. Non-complementing cell monolayers, typically in M24 well plates, 80% confluent, are infected with 10-fold dilutions of the arenavirus vector preparation for 90 min Subsequently, the cell layer is overlayed with suitable cell culture medium supplemented with 1% methylcellulose. Two to three days later, depending on the permissiveness of the non-complementing line used, the culture supernatant is removed, the cell layer is fixed, typically with ethanol/acetone or with formalin 4%, followed by permeabilization of the cell layer using mild detergents. Subsequently, arenavirus-vector-infected cell foci are identified using mono- or polyclonal antibody preparation(s) against one of the proteins in the arenavirus vector to be tested or against the antigen introduced. Bound antibody is detected using appropriate reagents, such as anti-isotype or anti-species antibodies that are conjugated to a system for visualization such as horse radish peroxidase, followed by a color reaction with suitable chromogens such as o-phenylenediamine. The resulting spots on the plate are counted to calculate the number of infectious focus forming units (FFU) per volume of arenavirus vector preparation (see, e.g., Flint, S. J.; Enquist, W., Racaniello, V. R., and Skalka, A. M. (2009). "Virological Methods". Principles of Virology. ASM Press. ISBN 1-55581-443-3).

Furthermore, plaque-based assays are the standard method used to determine virus concentration in terms of plaque forming units (PFU) in a virus sample. Specifically, a confluent monolayer of non-complementing host cells is infected with the virus at varying dilutions and covered with a semi-solid medium, such as agar to prevent the virus infection from spreading indiscriminately. A viral plaque is formed when a virus successfully infects and replicates itself in a cell within the fixed cell monolayer (see, e.g., Kaufmann, S. H.; Kabelitz, D. (2002). Methods in Microbiology Vol. 32: Immunology of Infection. Academic Press. ISBN 0-12-521532-0). Plaque formation can take 3-14 days, depending on the virus being analyzed. Plaques are generally counted manually and the results, in combination with the dilution factor used to prepare the plate, are used to calculate the number of plaque forming units per sample unit volume (PFU/mL). The PFU/mL result represents the number of infective replication-competent particles within the sample.

(f) Assay for Expression of Viral Antigen

Any assay known to the skilled artisan can be used for measuring expression of viral antigens. For example, Enzyme-Linked Immunosorbent Assay (ELISA) is a more modern variation of a protein assay that utilizes a specific antibody linked to an enzyme to detect the presence of an unknown amount of antigen (i.e. virus) in a sample. The antibody-antigen binding event is detected and/or quantified through the enzyme's ability to convert a reagent to a detectable signal that can be used to calculate the concentration of the antigen in the sample (see, e.g., Kemeny, D. M.; Challacombe, S. J. (1988). ELISA and Other Solid Phase Immunoassays: Theoretical and Practical Aspects. John Wiley and Sons. ISBN 0-471-90982-3). Horseradish peroxidase (HRP) is a common enzyme utilized in ELISA schemes due to its ability to amplify signal and increase assay sensitivity. There are many variations, or types of ELISA assays but they can generally be classified as either indirect, competitive, sandwich or reverse (e.g., Kuby, J.; Kindt, T. J., Goldsby, R. A., Osborne, B. A. (2007). Kuby Immunology 6th edition. W.H. Freeman and Company. ISBN 1-4292-0211-4). ELISA kits are commercially available from numerous companies and quantification generally occurs via chromogenic reporters or fluorescence (e.g., Invitrogen, Santa Cruz Biotechnology Inc.). This technique is much less labor intensive than the traditional methods and can take anywhere from 4 to 24 hours based on antibody incubation time.

(g) Animal Models

The safety, tolerance and immunogenic effectiveness of vaccines comprising of an infectious, replication-deficient arenavirus expressing a mycobacterial antigen described herein or a composition thereof can be tested in animals models. In certain embodiments, the animal models can be used to test the safety, tolerance and immunogenic effectiveness of the vaccines and compositions thereof used herein include mouse, guinea pig, rabbit, and monkeys (see, e.g., Gupta U. D. and Katock V. M., Tuberculosis. 2005; 85:277-293). In a preferred embodiment, the animal models that can be used to test the safety, tolerance and immunogenic effectiveness of the vaccines and compositions thereof used herein include mouse.

7. EXAMPLES

These examples demonstrate that replication-deficient lymphocytic choriomeningitis virus-based vector technology (rLCMV) can be successfully used to develop new vaccines against mycobacterial infection with *Mycobacterium tuberculosis* by including mycobacterial antigens into the arenavirus vector, and that administration of such vaccines can induce plurifunctional (IFN-γ and TNF-α co-producing) Mtb-specific CD4+ and CD8+ T cell responses of high magnitude to control *Mycobacterium tuberculosis* infection.

7.1 Design of Arenavirus Vector Genome

Ag85B and TB10.4 (SEQ ID NOs.: 4 and 5), which are both frequent targets of T cells in Mtb-infected human patients, were included in the rLCMV for creating the vaccine vector. Following established approaches (U.S. Patent Application Publication No. US 2010/0297172 A1; and Flatz L. et al., Nat Med. 2010 March; 16(3): 339-345) an rLCMV vaccine vector expressing a fusion antigen consisting of the Mtb antigens Ag85B and TB10.4 (rLCMV/Ag85B-TB10.4, FIG. 1) was designed. Redirection of Ag85B-TB10.4 intracellularly to a different compartment—namely to the endoplasmic reticulum—enhances the vaccine's immunogenicity was demonstrated herein. For this purpose an N-terminal signal sequence was attached to the Ag85B-TB10.4 gene. The signal sequence was taken from the tissue plasminogen activator (tPA) (SEQ ID NOs.: 6 and 7) and the resulting artificial open reading frame was therefore referred to as tPA-Ag85B-TB10.4 (SEQ ID NO: 2). The corresponding rLCMV vector (rLCMV/tPA-Ag85B-TB10.4) was also generated (SEQ ID NO: 1). Both vectors were produced and titrated according to established methodology (U.S. Patent Application Publication No. US 2010/0297172 A1; and Flatz L. et al., Nat Med. 2010 March; 16(3): 339-345).

7.2 Comparison of Immunogenicity and Functionality of rLCMV/tPA-Ag85B-TB10.4 and rLCMV/Ag85B-TB10.4 Vaccine Vectors in Mice Next, the immunogenicity of rLCMV/Ag85B-TB10.4 and rLCMV/tPA-Ag85B-TB 10.4 were analyzed and compared in mice (FIG. 2).

On day 0 of the experiment, C57BL/6 mice were immunized with $2\times10^5$ PFU of either rLCMV/tPA-Ag85B-TB10.4 (group 1) or rLCMV/Ag85B-TB10.4 (group 2) intravenously. Control mice were not immunized (group 3). The same immunization was repeated on day 28. On day 27 (panel A) and on day 38 (panel B) TB10.4 (IMYNYPAM)-specific CD8+ T cells were measured in peripheral blood by flow cytometry using MHC class I dextramers. The Dextramer-binding cells are expressed as percentage of the total CD8+ population (X in panels A and B). On day 56 of the experiment, the animals were euthanized and single cell suspensions were prepared from the spleen of the animals. These cells were stimulated with the TB10.4-derived QIMYNYPAM peptide comprising of SEQ ID NO:10 and the Ag85B-derived THSWEYWGAQLNAMKGDLQS peptide comprising of SEQ ID NO: 8 to determine antigen-specific interferon-γ (IFN-γ) and tumor necrosis factor-α (TNF-α) co-producing CD8+ (panel C), as well as IFN-γ and TNF-α co-producing CD4+ T cells (panel D), respectively. For this, standard intracellular cytokine staining and flow cytometry techniques were used. IFN-γ and TNF-α co-producing cells amongst total CD8+ T cells (Y in panel C) or amongst total CD4+ T cells (Z in panel D) are expressed as a percentage. Symbols represent individual mice. Group 1 and group 2 mice were significantly different in all measurements as determined using unpaired two-tailed student's t-test (p=0.0226, p=0.0108, p=0.0044, p=0.0001 in panels A-D, respectively).

After a single intravenous immunization (prime), both vectors induced Mtb-specific CD8+ T cell responses of very considerable magnitude (FIG. 2A). These responses was efficiently augmented when the same vector was re-administered four weeks after prime (boost, FIG. 2B). After prime as well as after boost, rLCMV/tPA-Ag85B-TB10.4 induced significantly stronger responses than rLCMV/Ag85B-TB10.4. The functionality of CD8+ and CD4+ T cell responses after prime-boost vaccination was investigated. Both vectors induced plurifunctional IFN-γ and TNF-α co-producing CD8+ (FIG. 2C) and CD4+ T cell responses (FIG. 2D) of high magnitude. In analogy to the differences in strength of total Mtb-specific CD8+ T cell responses (FIG. 2A, B), plurifunctional CD8+ and CD4+ T cell responses to rLCMV/tPA-Ag85B-TB10.4 were of significantly higher magnitude than those elicited by rLCMV/Ag85B-TB10.4. These data demonstrated that a modification of the intracellular targeting of Ag85B-TB10.4 by means of an N-terminal leader peptide such as the one of tPA can augment CD8+ and CD4+ T cell responses.

7.3 Comparison of Immunogenicity of rLCMV/tPA-Ag85B-TB10.4 Vaccine Vector Administered by Intravenous or Subcutaneous Routes Next, the immunogenicity of rLCMV/tPA-Ag85B-TB10.4 when administered subcutaneously to mice was compared to the responses elicited by intravenous immunization with the same vector (FIG. 3).

On day 0 of the experiment, C57BL/6 mice were immunized with $10^5$ PFU of rLCMV/tPA-Ag85B-TB10.4 either via the intravenous route (group 1) or by the subcutaneous route (group 2). Control mice were not immunized (group 3). On day 11, the animals were euthanized and single cell suspensions were prepared from the spleen of these animals. TB10.4 (IMYNYPAM (SEQ ID NO:9))-specific CD8+ T cells were measured by flow cytometry using MHC class I dextramers. The Dextramer-binding cells are expressed as percentage of the total CD8+ population (X in panels A). The spleen cells were also stimulated with TB10.4-derived QIMYNYPAM peptide comprising of SEQ ID NO:10 and the Ag85B-derived THSWEYWGAQLNAMKGDLQS peptide comprising of SEQ ID NO: 8 to determine antigen-specific IFN-γ producing CD8+ (panel B), as well as IFN-γ and TNF-α co-producing CD4+ T cells (panel C), respectively. For this, standard intracellular cytokine staining and flow cytometry techniques were used. Epitope-specific IFN-γ producing CD8+ T cell within the total CD8+ T cells (Y in panel B), as well as IFN-γ and TNF-α co-producing cells amongst total CD4+ T cells (Z in panel C), are expressed as a percentage. Symbols represent individual mice.

The total magnitude of Mtb-specific CD8 T cell responses (FIG. 3A) as well as the magnitude of Mtb-specific plurifunctional CD8+ (FIG. 3B) and CD4+ (FIG. 3C) T cells was assessed. These analyses demonstrated that rLCMV/tPA-Ag85B-TB10.4 induced high frequency plurifunctional CD8+ and CD4+ T cell responses irrespective the route of vaccine administration.

7.4 Immunization Studies with rLCMV/tPA-Ag85B-TB10.4 Vaccine Vector in Adult and 1-Week-Old Mice The capacity of rLCMV/tPA-Ag85B-TB10.4 for inducing Mtb-specific CD8+ and CD4+ T cells in one week-old mice was examined, and these responses were compared to those of adult animals (FIG. 4).

On day 0 of the experiment, adult (group 1) and 1-week-old (group 2) C57BL/6 mice were immunized with $10^5$ PFU of rLCMV/tPA-Ag85B-TB10.4 via the subcutaneous route. On day 10, the animals were euthanized and single cell suspensions were prepared from the spleen of these animals. TB10.4 (IMYNYPAM (SEQ ID NO:9))-specific CD8+ T cells were measured by flow cytometry using MHC class I dextramers. The Dextramer-binding cells are expressed as percentage of the total CD8+ population (X in panels A) or as total number of Dextramer-binding CD8+ cells in spleen (Y in panel B). These spleen cells were also stimulated with the TB10.4-derived QIMYNYPAM peptide comprising of SEQ ID NO:10 and the Ag85B-derived THSWEYWGAQLNAMKGDLQS peptide comprising of SEQ ID NO: 8 to determine antigen-specific interferon-γ (IFN-γ) and tumor necrosis factor-α (TNF-α) co-producing CD8+ (panel C), as well as IFN-γ and TNF-α co-producing CD4+ T cells (panel D), respectively. For this, standard intracellular cytokine staining and flow cytometry techniques were used. IFN-γ and TNF-α co-producing cells amongst total CD8+ T cells (Z in panel C) or amongst total CD4+ T cells (XY in panel D) are expressed as a percentage. Symbols represent individual mice.

The magnitude of Mtb-specific CD8+ T cell responses was equivalent in one week-old and adult mice. Importantly, not only the relative proportion of specific CD8+ T cells (FIG. 4A), but also their total number (FIG. 4B) was in the same range. Mtb-specific CD8+ cells of rLCMV/tPA-Ag85B-TB10.4-vaccinated one week-old mice were as functional as those of adult mice, which was evident from an equivalent capacity to co-produce IFN-γ and TNF-α. Furthermore, one-week-old and adult mice mounted comparable plurifunctional Mtb-specific CD4+ T cell responses (FIG. 4D). These findings demonstrated the capacity of rLCMV/tPA-Ag85B-TB10.4 to induce plurifunctional Mtb-specific CD8+ and CD4+ T cell responses in very young, and therefore, immunologically still immature individuals.

What is claimed is:

1. An infectious, replication-deficient arenavirus particle comprising a nucleotide sequence encoding a mycobacterial antigen, wherein the mycobacterial antigen is a fusion protein comprising Ag85B or an antigenic fragment thereof and TB10.4 or an antigenic fragment thereof wherein the mycobacterial antigen is fused to a signal peptide of a tissue plasminogen activator, and wherein the signal peptide of a tissue plasminogen activator comprises the amino acid sequence of SEQ ID NO:7.

2. An infectious, replication-deficient arenavirus particle comprising a nucleotide sequence encoding a mycobacterial antigen, wherein the mycobacterial antigen is a fusion protein comprising Ag85B or an antigenic fragment thereof and TB10.4 or an antigenic fragment thereof wherein the mycobacterial antigen is fused to a signal peptide of a tissue plasminogen activator, and wherein the infectious, replication-deficient arenavirus particle comprises a genomic segment, wherein the genomic segment comprises a nucleotide sequence that is at least 98%, 99%, or 100% identical to SEQ ID NO:1.

3. An isolated nucleic acid, wherein the isolated nucleic acid encodes an arenavirus genomic segment of an arenavirus, wherein one open reading frame of the genomic segment is deleted or functionally inactivated, wherein the genomic segment encodes a mycobacterial antigen, wherein the mycobacterial antigen is a fusion protein comprising Ag85B or an antigenic fragment thereof and TB10.4 or an antigenic fragment thereof, and wherein the mycobacterial antigen is fused to a signal peptide of a tissue plasminogen activator, and wherein the isolated nucleic acid comprises a nucleotide sequence that is at least 98%, 99%, or 100% identical to SEQ ID NO:1.

* * * * *